US012655113B2

(12) United States Patent
Riva et al.

(10) Patent No.: US 12,655,113 B2
(45) Date of Patent: Jun. 16, 2026

(54) BIPHENYL COMPOUNDS AS SOCE MODULATORS, COMPOSITIONS AND USES THEREOF

(71) Applicant: Università degli Studi del Piemonte Orientale "Amedeo Avogadro", Vercelli (IT)

(72) Inventors: Beatrice Riva, Cerrione (IT); Tracey Pirali, Novara (IT); Marta Serafini, Gattinara Vercelli (IT); Silvio Aprile, Prato Sesia (IT); Celia Cordero Sanchez, Novara (IT); Ambra Grolla, Castano Primo (IT)

(73) Assignee: UNIVERSITÀ DEGLI STUDI DEL PIEMONTE ORIENTALE "AMEDEO AVOGADRO", Vercelli (IT)

(*) Notice: Subject to any disclaimer, the term of this patent is extended or adjusted under 35 U.S.C. 154(b) by 852 days.

(21) Appl. No.: 17/801,183

(22) PCT Filed: Nov. 25, 2020

(86) PCT No.: PCT/IB2020/061136
§ 371 (c)(1),
(2) Date: Aug. 19, 2022

(87) PCT Pub. No.: WO2021/165735
PCT Pub. Date: Aug. 26, 2021

(65) Prior Publication Data

US 2023/0348404 A1 Nov. 2, 2023

(30) Foreign Application Priority Data

Feb. 21, 2020 (IT) ........................ 102020000003692

(51) Int. Cl.

| | |
|---|---|
| ***C07D 249/06*** | (2006.01) |
| ***C07D 401/04*** | (2006.01) |
| ***C07D 405/10*** | (2006.01) |
| ***C07D 405/14*** | (2006.01) |

(52) U.S. Cl.
CPC ......... *C07D 249/06* (2013.01); *C07D 401/04* (2013.01); *C07D 405/10* (2013.01); *C07D 405/14* (2013.01)

(58) Field of Classification Search
CPC .. C07D 401/04; C07D 249/06; C07D 405/10; C07D 405/14; A61P 25/00; A61P 37/00
See application file for complete search history.

(56) References Cited

U.S. PATENT DOCUMENTS

| | | | |
|---|---|---|---|
| 2010/0105689 A1 | 4/2010 | Nardi et al. | |
| 2014/0005231 A1 | 1/2014 | Bereznak et al. | |
| 2019/0300509 A1 | 10/2019 | Pirali et al. | |

FOREIGN PATENT DOCUMENTS

| | | | |
|---|---|---|---|
| CN | 104603128 A | 5/2015 | |
| EP | 2 578 581 | 4/2013 | |
| EP | 2578581 A1 * | 4/2013 | ........... C07D 403/04 |
| JP | 2020055768 A | 4/2020 | |
| WO | 2014004064 A1 | 1/2014 | |
| WO | 2017/212414 | 12/2017 | |

OTHER PUBLICATIONS

Chen, et al.; Biochimica et Biophysica Acta, v1863, pp. 1427-1435; 2016 (Year: 2016).*
Crusz, S. and Balkwill, F.R.; Nature Reviews Clinical Oncology, v12, pp. 584â596; 2015 (Year: 2015).*
Diaz-Marta, et al.; ACS Appl. Mater. Interfaces, v11, pp. 25283-25294; 2019 (Year: 2019).*
Bhardwaj, et al.; Catalysis Letters, v146, pp. 629-644; 2016 (Year: 2016).*
Cho, et al.; Organic Letters, v11, pp. 4330-4333; 2009 (Year: 2009).*
Sang, et al.; Chemical Communications, v55, pp. 5886-5889; 2019 (Year: 2019).*
Brown; Bioisosteres in Medicinal Chemistry, Wiley-VCH, 2012 (Year: 2012).*
Wang, et al., Liquid Crystals, v46, pp. 257-271; 2019 (Year: 2019).*
Gilandoust, et al.; Bioorganic & Medicinal Chemistry Letters, v28, pp. 2314-2319; 2018 (Year: 2018).*
Antonio Sanchez Díaz-Marta, Multicatalysis Combining 3D-Printed Devices and Magnetic Nanoparticles in One-Pot Reactions: Steps Forward in Compartmentation and Recyclability of Catalysts, ACS Appl Mater Interfaces, vol. 11, No. 28, pp. 25283-25294, Jul. 17, 2019.

(Continued)

*Primary Examiner* — Jeffrey S Lundgren
*Assistant Examiner* — W. Justin Youngblood
(74) *Attorney, Agent, or Firm* — Nixon & Vanderhye, PC

(57) ABSTRACT

Compound of formula (I) able to modulate Store Operated Calcium Entry (SOCE). The disclosure also relates to compositions and uses of compounds of formula (I) for treatment of disease condition depending on increased/decreased activity of SOCE.

(I)

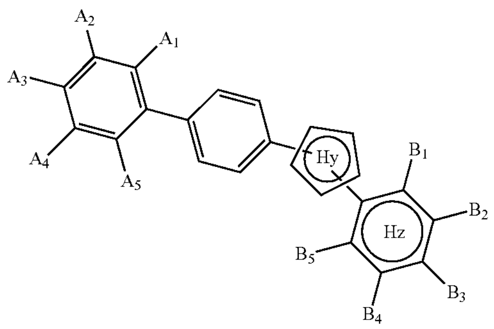

12 Claims, 5 Drawing Sheets

Specification includes a Sequence Listing.

(56) References Cited

OTHER PUBLICATIONS

Bhardwaj et al., Novel Cu(0)-$Fe_3O_4$@$SiO_2$/$NH_2$cel as an Efficient and Sustainable Magnetic Catalyst for the Synthesis of 1,4-Disubstituted-1,2,3-triazoles and 2-Substituted-Benzothiazoles via One-Pot Strategy in Aqueous Media, Catalysis Letters, vol. 146, pp. 629-644, Jan. 2016.
Colombano et al., A novel potent nicotinamide phosphoribosyltransferase inhibitor synthesized via click chemistry, J Med Chem., vol. 53, No. 2, pp. 616-623, Jan. 28, 2010.
Sang et al., Efficient discovery of novel antimicrobials through integration of synthesis and testing in crude ribosome extract, Chem. Commun, 55, pp. 5886-5889, 2019.
Susmita Roy et al., Cu(II)-anchored functionalized mesoporous SBA-15: An efficient and recyclable catalyst for the one-pot Click reaction in water, Journal of Molecular Catalysis A: Chemical, vol. 386, pp. 78-85, May 2014.
Wang et al., The synthesis of [1,2,3]-triazole-based bent core liquid crystals via microwave-mediated 'Click Reaction' and their mesomorphic behaviour, Liquid Crystals, vol. 46, Issue 2, 15 pages, 2018.
Cho, Y.E. et al., "Preparation of Potassium Azidoaryltrifluoroborates and Their Cross-Coupling with Aryl Halides" Oct. 1, 2009. Organic Letters, vol. 11., No. 19, pp. 4330-4333 (5 pages).
Bolla, K. et al., "Efficient and rapid synthesis of regioselective functionalized potassium 1,2,3-triazoletrifluoroborates via 1,3-dipolar cycloaddition" May 30, 2011, Tetrahedron, Elsevier Science Publishers, vol. 67, No. 31, pp. 5556-5563 (8 pages).
Gilandoust, M. et al., "Synthesis, characterization and cytotoxicity studies of 1,2,3-triazoles and 1,2,4-triazolo [1,5-a] pyrimidines in human breast cancer cells" Jul. 1, 2018, Bioorganic & Medicinal Chemistry Letters, vol. 28, No. 13, pp. 2314-2319 (5 pages).
Baschieri, A. et al., "Introducing a New Family of Biotinylated Ir{III)-Pyridyltriazole Lumophores: Synthesis, Photophysics, and Preliminary Study of Avidin-Binding Properties" Oct. 7, 2014, Organometallics, Vo. 33, No. 21, pp. 6154-6164 (11 pages).
International Search Report and Written Opinion of the ISA for PCT/IB2020/061136, dated Mar. 3, 2021 (13 pages).

* cited by examiner

A

B

BIPHENYL COMPOUNDS AS SOCE MODULATORS, COMPOSITIONS AND USES THEREOF

This application is the U.S. national phase of International Application No. PCT/IB2020/061136 filed Nov. 25, 2020 which designated the U.S. and claims priority to IT 102020000003692 filed Feb. 21, 2020, the entire contents of each of which are hereby incorporated by reference.

FIELD OF THE INVENTION

The disclosure concerns new biphenyl 1,4-disubstituted 1,2,3-triazol compounds able to modulate the calcium entry operated by endoplasmic reticulum, also known as Store-Operated Calcium Entry (SOCE), compositions, and uses thereof.

BACKGROUND OF THE INVENTION

Calcium ($Ca^{2+}$) represents a ubiquitous messenger serving as universal signal molecule to codify information between and inside the cells, regulating a wide range of cellular functions ranging from short-term responses, such as contraction and secretion, to longer-term control of transcription, cell division and cell death (Jeremy T. Smyth, et al.; 2010. J. Cell. Mol. Med. Vol 14, No 10, pp. 2337-2349; Lewis Richard S. 2011Cold Spring Harb Perspect Biol; 3: a003970). The huge gradient across the cell plasma membrane together with the very low concentration of $Ca^{2+}$ in the cytosol ($Ca^{2+}$ is $10^5$ times more abundant in organelles and in the extracellular medium) became thereafter a great opportunity to use this ion as a specific second messenger. A $Ca^{2+}$-signal codifies a message through the exact spatial localization in the cell, the amplitude, the duration and the frequency of its rise. High concentrations of calcium ions are present in intracellular organelles (in particular in the endoplasmic reticulum (ER) and/or sarcoplasmic reticulum (SR)) and the opening of $Ca^{2+}$-channels (e.g. RyR, IP3R) located on these membranes allows this ion to flux out of the deposit and elicit cellular signals. Although $Ca^{2+}$-pumps that are able to re-uptake $Ca^{2+}$ are present on the SR/ER membranes, it would be expected that this organelle would be soon depleted of $Ca^{2+}$ given the activity of plasma membrane efflux mechanisms. This is not the case since in the cell there is a cross-talk between the ER and the plasma membrane, represented by the so named Store-Operated $Ca^{2+}$-entry (SOCE). The term SOCE is referred to the ability of cells to sense a decrease of calcium concentration in the ER and to induce a flux of this ion across the plasma membrane into the cell (Putney J W. 2011. Frontiers in Bioscience (Scholar Edition) 3:980-984).

SOCE is associated with the electrophysiological current $I_{CRAC}$, firstly described by Hoth and Penner (Hoth M, Penner R. 1992. Nature 355:353-356). The exact molecular mechanism behind this phenomenon has been elucidated between 2005 and 2006, when the principal components of the SOCE machinery, the $Ca^{2+}$-Release Activated-$Ca^{2+}$ (CRAC) channels, have been discovered. CRAC channels are assembled from two fundamental protein complexes: Orai proteins that form the ion channel pore on the plasma membrane, and the Stromal Interaction Molecule (STIM) proteins, which act as calcium sensors on the ER. (Berna-Erro A, et al. Redondo P C, Rosado J A. 2012 Medicine and Biology 740:349-382; Soboloff J, Rothberg B S, Madesh M, Gill D L. 2012 Nature Reviews. Molecular Cell Biology 13:549-565; Lacruz R S, Feske S. 2015. Annals of the New York Academy of Sciences 1356:45-79). Besides STIM and Orai, it should be underlined that other crucial proteins participate in the SOCE mechanism, including Transient Receptor Potential Channels (TRPCs) (Ong H L, Ambudkar I S. 2015. Cell Calcium 58:376-386).

STIM proteins are single-span membrane proteins, highly conserved across species. Two members of the family have been described, STIM1 and STIM2, of which the former appears more expressed (Roos et al. (2005; J Cell Biol.; 169(3):435-45.) Using a limited RNAi screen of *Drosophila* S2 cells *Drosophila* STIM was identified as having a fundamental role in SOCE activation, and a similar conclusion was reached almost concurrently for human STIM1 and STIM2 in a HeLa cell screen (Jeremy T. Smyth, et al.; 2010. J. Cell. Mol. Med. Vol 14, No 10, pp. 2337-2349, Lewis Richard S. 2011 Cold Spring Harb Perspect Biol; 3: a003970). STIM1 was identified as a $Ca^{2+}$ sensor for SOCE since it is specialized for responding to significant changes in ER $Ca^{2+}$ signals. STIM1 localization is crucial to the role of SOCE: when $Ca^{2+}$ stores are full, STIM1 is localized in tubular structures throughout the ER membrane, but when stores are depleted it moves to punctate structures at sites where the ER is in contact with the plasma membrane. This re-localization of STIM1 within the ER towards the plasma membrane allows the direct or indirect interaction and activation of Orai channels. Orai channels reside on the plasma membrane and three members of the family (Orai 1, Orai 2, and Orai 3) have been described, with Orai 1 being the most abundant and closely connected to the $I_{CRAC}$ (Jeremy T. Smyth, et al.; 2010. J. Cell. Mol. Med. Vol 14, No 10, pp. 2337-2349; Lewis Richard S. 2011 Cold Spring Harb Perspect Biol, 3: a003970; Feske S. et al 2005 J Exp Med 202(5):651-62; Nature 11; 441(7090):179-85.).

The key experiment to exemplify SOCE is depicted in FIG. 1. Briefly, emptying of the ER/SR store leads to opening of a channel located on the plasma membrane through which $Ca^{2+}$ can flow back in the cell and these two phenomena can be dissected by adding $Ca^{2+}$ to the extracellular solution after the intracellular stores are depleted. This simple, yet powerful, in vitro experimental approach remains valid to unmask the phenomenon in screenings.

CRAC currents were initially identified in lymphocytes and mast cells, and simultaneously characterized in different cell lines such as DT40 B cells, hepatocytes, dendritic, megakaryotic and Madin-Darby canine kidney cells. In lymphocytes and mast cells, the activation through T-cell receptor or Fc receptor initiates the release of $Ca^{2+}$ ion from intracellular stores caused by the second messenger inositol (1,4,5)-triphosphate ($IP_3$), that leads to $Ca^{2+}$ ion influx through CRAC channels in the plasma membrane.

CRAC channels also mediate crucial functions from secretion to gene expression and cell growth and form a process essential for the activation of adaptive immune response. It has been demonstrated that $Ca^{2+}$ oscillations triggered through stimulation of the T-cell antigen receptor (TCR) involved only the influx pathway of the store operated CRAC channel. Therefore, $Ca^{2+}$ ion influx mediated by the store operated CRAC channel is fundamental in lymphocyte activation (Anant B. Parekh and James W. Putney Jr. 2005, Physiol Rev 85: 757-810.; Hogan G. p., et al 2010, Annu. Rev. Immunol. 28:491-533; Patrick G Hogan and Anjana Rao 2015, Biochem Biophys Res Commun 24, 460(1): 40-49.; Feske S, Okamura H, Hogan P G, Rao A. 2003, Biochem Biophys Res Commun, 311(4):1117-32.). Conversely, the store-operated $Ca^{2+}$ currents identified in endothelial cells, smooth muscle, epidermal cells and prostate cancer cells lines show altered biophysical characteristic suggesting a different molecular origin. These evidences demonstrate that intracellular $Ca^{2+}$ plays an important role in different cellular functions, and its concentration by $Ca^{2+}$ influx through $Ca^{2+}$ channels on the plasma membrane and ER.

In skeletal muscles from patient suffering of Duchenne Muscular Dystrophy (DMD) and from mdx mouse (a popular model for studying DMD that has a point mutation in its DMD gene), the absence of the cytoskeleton protein dystrophin has been shown to be essential for maintaining a normal calcium influx. In particular, it has been reported that STIM1, ORAI 1 and TRPC1 store-dependent influx is increased by loss of dystrophin, suggesting an involvement of SOCE in this lethal pathology (Onopiuk M. 2015 Arch Biochem Biophys, 569:1-9; Sabourin J. 2012 Cell Calcium, 6:445-456).

Furthermore, the pivotal role played by CRAC channels in human health is underlined by an increasing list of genetic studies that led to the identification of patients bearing loss- or gain-of-function STIM1/Orai 1 mutations that are affected by severe health issues, such as muscle defects, immunodeficiency, autoimmunity and bleeding disorders (Feske S. 2010 European Journal of Physiology, 460:417-435).

Regarding loss-of-function mutations, at least three unrelated families have been described that, due to different mutations, including frame-shifts, do not express Orai 1 on the plasma membrane of T-lymphocytes, lack store-operated $Ca^{2+}$-entry and are thereby unable to activate T-lymphocytes (Feske S, et al. 1996 European Journal of Immunology 26:2119-2126; McCarl C A, et al. 2009. J Allergy Clin Immunol. 124(6):1311-1318. e7.) Notably, families with STIM1 mutations that lead to no expression of the protein have been reported and are characterized by a T-cell immunodeficiency (Picard C, et al. 2009, N Engl J Med. 7, 360(19):1971-80; Byun M, et al. 2010, The Journal of Experimental Medicine, 207:2307-2312; Fuchs S, et al. 2012 Journal of Immunology (Baltimore, Md.: 1950) 188: 1523-1533). Last, while immunodeficiency is the hallmark of the disease, these patients also display lymphoproliferative diseases, autoimmunity, congenital myopathy, anhidrosis, tooth enamel, and an impairment in thrombus formation due to a defect in platelet activation. While some mutations give rise to a decreased activity that might be potentiated pharmacologically, most mutations yield a significant decrease in protein expression and therefore pharmacological approaches might be indicated also for these disorders. Currently, the loss-of-function mutations of STIM1 and Orai 1 reported in the literature are the following: p.P165Q, p.R429C, p.R426C, p.E128RfsX9 for STIM1, and p.R91W, p.A103E, p.L194P, p.A88SfsX25 and p.H165PfsX1 for Orai 1.

Gain-of-function mutations of STIM1 or Orai 1 affect primarily skeletal muscles and platelets, although it appears to be a multi-organ disease (Lacruz R S, Feske S. 2015. Annals of the New York Academy of Sciences 1356:45-79). The prevalence of the disorders is unknown, but it is likely that their aggregate prevalence is approximately 1/250,000. Given the rarity of the disorder, compared to other myopathies, the disorder has not been tackled systematically in the clinic and disease registries are not available at present. Both STIM1 and Orai 1 mutations are linked to the three separate but overlapping, disorders: tubular aggregate myopathy, Stormorken syndrome and York platelet syndrome. Tubular aggregate myopathy is characterized by variable combinations of myalgias, cramps and muscle stiffness, with or without weakness with a predominantly proximal distribution and the presence of tubular aggregates, which are regular arrays of tubules derived from the sarcoplasmic reticulum (Böhm J, et al. 2013. American Journal of Human Genetics 92:271-278; Nesin V, et al. 2014. Proceedings of the National Academy of Sciences of the United States of America 111:4197-4202; Endo Y, et al. 2015. Human Molecular Genetics 24:637-648.). Stormorken syndrome is characterized by the myopathic signs, but may also include mild bleeding tendency due to platelet dysfunction, thrombocytopenia, anemia, asplenia, congenital miosis, ichthyosis, headache and recurrent strokelike episodes (Stormorken H, et al. 1995. Thromb Haemost 74:1244-1251). Last, York platelet syndrome sees blood dyscrasias as the main phenotype. Currently, the gain-of-function mutations of STIM1 and Orai 1 reported in the literature are the following: p.N80T, p.H72Q, p.G81D, p.D84G, p.D84E, p.L96V, p.F108L, p.F108I, p.H109R, p.H109N, p.I115F, p.R304W, p.R304G for STIM1; and p.S97C, p.G98S, p.V107M, p.L138F, p.T184M, p.P245L for Orai 1. Briefly, mutations of STIM1 mostly reside in the EF-hand $Ca^{2+}$-binding motifs, most likely modifying the affinity for $Ca^{2+}$ ions of the protein, with the single exception of a mutation located in the cytosolic side of the protein on a coil-coiled domain that is likely to affect dimerization/oligomerization of STIM1, a putative trigger of Orai 1 channel opening. The mutations of Orai 1 are located in the trans-membrane domains in positions that might lead to the assumption that they participate in the channel lining.

All these data suggest that modulators of SOCE would be useful for the treatment of diseases caused by an abnormal SOCE. A key limitation in the study of SOCE and its physio- and pathophysiological role is the lack of potent and selective modulators.

Synta66 (GSK1349571A; 3-fluoropyridine-4-carboxylic acid (2',5'-dimethoxybiphenyl-4-yl)amide) is a compound developed by Synta Pharmaceuticals and GSK. It inhibits $I_{CRAC}$ with an $IC_{50}$ of around 1 μM (Di Sabatino A. 2009. Journal of Immunology (Baltimore, Md.: 1950) 183:3454-3462; Ng, S. W. Journal of Biological Chemistry, 2008, 283, 31348-31355; WO2005009954; WO2005009539). Moreover, it is reported that it is able to decrease T cell cytokine production and, in particular, it inhibits the production of IFN-gamma, IL-2 and IL-17, but not of IL-8 (Di Sabatino A. 2009. Journal of Immunology (Baltimore, Md.: 1950) 183: 3454-3462). Interestingly, in vascular smooth muscle cells the potency is of two orders of magnitude greater ($IC_{50}$ around 30 nM) (Li, J. BJP, 2011, 164, 382-393).

The detailed mechanism of the compound is unknown, though siRNA knockdown of Orai 1 in mast cells suggests that it might be selective for Orai 1 (Ng, S. W. Journal of Biological Chemistry, 2008, 283, 31348-31355). Furthermore, experiments in vascular smooth muscle cells suggest that it does not interfere with STIM1 clustering, raising the possibility that the drug does not target STIM1 mechanism (Li, J. BJP, 2011, 164, 382-393).

It has been reported that Synta66 does not affect metabotropic glutamate, muscarinic acetylcholine and GABA B receptors, GABA A, AMPA and NMDA receptors, ligand gated ion channels such as tetrodotoxin-sensitive $Na^{+}$ channels, and N- and P/Q-type voltage-gated $Ca^{2+}$ channels (Di Sabatino A. 2009. Journal of Immunology (Baltimore, Md.: 1950). Moreover, it does not inhibit endogenous TRPC1/5 or overexpressed TRPC5 channels (Li, J. BJP, 2011, 164, 382-393).

An increasing number of studies are employing Synta66 for investigating the physiological role of CRAC channels in vitro and in animal models; however, its specificity over the different Orai isoforms is not optimal.

WO 2017/212414 discloses 5-(trifluoromethyl)-1H-pyrazoles with at 1-position a phenyl ring carrying a triazole in para-position as SOCE modulators.

Young Ae Cho et al, *Organic Letters* (2009) 11(19):4330-4333 disclose the synthesis of 4'-(4-phenyl-1H-1,2,3-triazol-1-yl)-[1,1'-biphenyl]-4-carbonitrile.

K. Bolla et al, *Tetrahedron* (2011) 67(31):5556-5563 disclose the synthesis of 4'-(4-phenyl-1H-1,2,3-triazol-1-yl)[1,1'-biphenyl]-4-carbonitrile, 1-(4'-methoxy-[1,1'-biphenyl]-4-yl)-4-phenyl-1H-1,2,3-triazole, and 2-(4-(4-phenyl-1H-1,2,3-triazol-1-yl)phenyl)pyridine.

M. Gilandoust et al, *Bioorganics & Medicinal Chemistry Letters* (2018) 28(13):2314-2319 disclose 1-(2'-ethoxy-4'-fluoro-[1,1'-biphenyl]-4-yl)-4-phenyl-1H-1,2,3-triazole, 2-fluoro-5-(4-(4-phenyl-1H-1,2,3-triazol-1-yl)phenyl)pyridine, 1-(3'-(methylsulfonyl)-[1,1'-biphenyl]-4-yl)-4-phenyl-1H-1,2,3-triazole, 5-(4-(4-phenyl-1H-1,2,3-triazol-1-yl) phenyl)nicotinonitrile, 1-(2'-chloro-[1,1'-biphenyl]-4-yl)-4-phenyl-1H-1,2,3-triazole, 1-(5'-chloro-2'-fluoro-[1,1'-biphenyl]-4-yl)-4-phenyl-1H-1,2,3-triazole, 1-(5'-fluoro-2'-methoxy-[1,1'-biphenyl]-4-yl)-4-phenyl-1H-1,2,3-triazole, and 1-([1,1'-biphenyl]-4-yl)-4-phenyl-1H-1,2,3-triazole as cytotoxic agents against human breast cancer cells.

A. Baschieri et al, *Organometallics* (2014) 33(21):6154-6164 disclose the synthesis of 4'-(4-(pyridin-2-yl)-1H-1,2,3-triazol-1-yl)-[1,1'-biphenyl]-4-amine, and 4'-(4-(pyridin-2-yl)-1H-1,2,3-triazol-1-yl)-[1,1'-biphenyl]-4-ol as intermediates for the production of luminescent compounds.

US 2014/005231 discloses N-(4'-(4-phenyl-1H-1,2,3-triazol-1-yl)-[1,1'-biphenyl]-2-yl)-2-(trifluoromethyl)benzamide, and N-(5-fluoro-4'-(4-phenyl-1H-1,2,3-triazol-1-yl)-[1,1'-biphenyl]-2-yl)-2-(trifluoromethyl)benzamide as fungicides and nematocides useful in the control of plant diseases.

EP 2578581 discloses the synthesis of 4-[4-(4-biphenyl-1H-1,2,3-triazol-1-yl]pyridine-2,6-dicarboxylic acid as intermediate for the production of luminescent compounds.

It is worth noting that, with the exception of the compounds disclosed in WO 2017/212414, none of the biphenyl 1,4-disubstituted 1,2,3-triazol compounds disclosed in the above mentioned prior art documents have been indicated as a SOCE modulator.

There remains an unmet need for small molecule modulators having high potency and specificity towards STIM1 and/or Orai 1 in order to regulate activity of CRAC channels, particularly for the treatment of diseases and disorders associated with SOCE.

SUMMARY OF THE INVENTION

The object of this disclosure is to provide new compounds able to modulate SOCE.

According to the invention, the above object is achieved thanks to the subject matter recalled specifically in the ensuing claims, which are understood as forming an integral part of this disclosure.

The present invention provides a class of compounds as novel SOCE modulators and their use in therapy. More particularly, the invention provides a family of biphenyl 1,4-disubstituted 1,2,3-triazol compounds.

The present disclosure discloses compounds of formula (I):

(I)

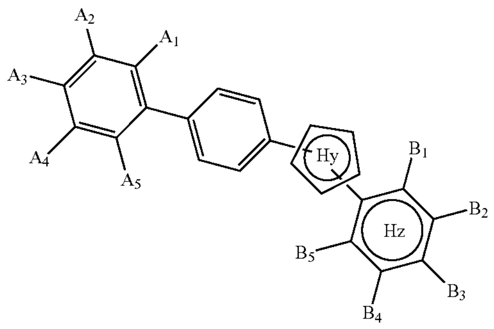

wherein ring Hy is selected from

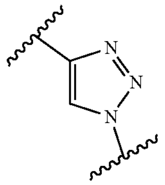

and

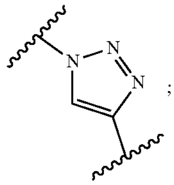

;

ring Hz is selected from a aryl or heteroaryl group;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHCOR_1$, $NHSO_2R_1$, $CONHR_1$, $CONR_1R_2$, $SO_2NHR_1$, COOH, $COOR_1$, $NO_2$, CN, a 5-6 membered O-heterocyclic group;

$A_1$ and $A_2$, or $A_2$ and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are independently selected from H, $CH_2COOH$, COOH, $COOR_3$, CN, $CF_3$, Br, I, Cl, F and 1H-tetrazol-5-yl;

$R_1$ and $R_2$ are identical or different from each other and independently selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;

$R_3$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$-$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heteroaryl, wherein m is an integer 1 to 4;

pharmaceutically acceptable hydrates and/or solvates and/or salts thereof.

The present disclosure discloses biphenyl 1,4-disubstituted 1,2,3-triazol compounds of formula (I) for use as a medicament, preferably with a specific activity on SOCE.

The present disclosure also discloses to the compounds of formula (I) for use in in vivo treatment of pathological conditions linked to loss- or gain-of-function STIM1/Orai 1 mutations, muscular dystrophies, inflammatory diseases, in which SOCE modulation is beneficial.

The present disclosure also discloses pharmaceutical compositions comprising at least one compound of formula (I) and a pharmaceutically acceptable carrier. The pharmaceutical composition may further comprise one or more additional therapeutic agents.

BRIEF DESCRIPTION OF THE DRAWINGS

The invention will now be described in detail, purely by way of illustrative and non-limiting example, with reference to the attached figures, wherein.

Experiments were carried out prior to and during exposure of the cells to the $Ca^{2+}$-free solution. In the absence of $Ca^{2+}$, the intracellular $Ca^{2+}$ stores were depleted by 2,5-t-butylhydroquinone (tBHQ, 50 μM; Sigma-Aldrich, Italy), a SERCA poison, and then calcium 2 mM was re-added to the extracellular solution.

Figure 2:
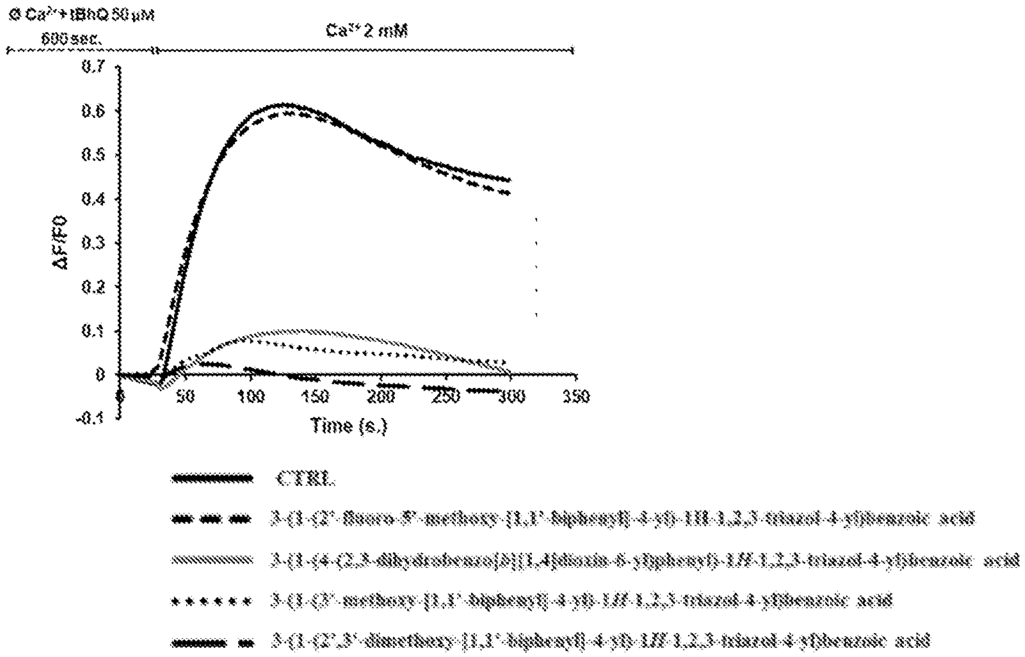
Figure 2:
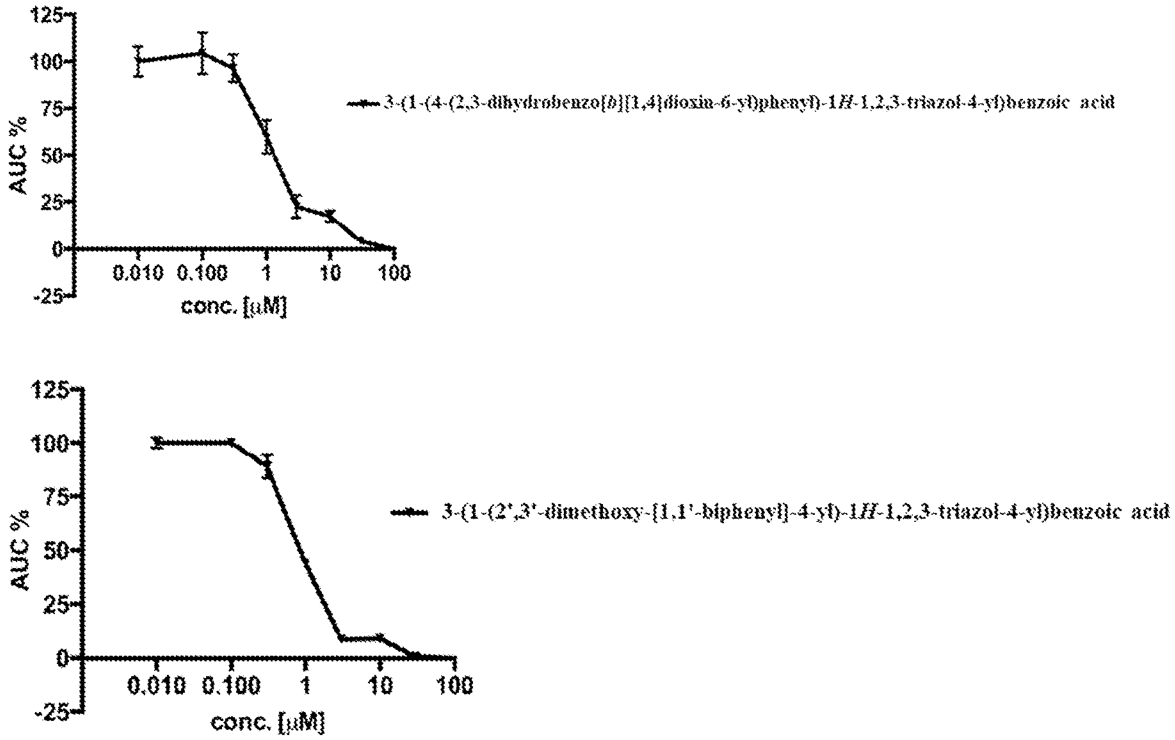

FIG. 2: Calcium response to SOCE-modulators.

(A) HEK cells were plated in poly-d-lysine coated 6-well plate and incubated overnight. After 24 hours, cells were loaded with 5 μM Fura-2 AM and placed in an extracellular solution containing 0 mM $Ca^{2+}$. Stores were depleted with 50 μM tBHQ and calcium influx was stimulated by the addition of 2 mM $Ca^{2+}$ alone (Ctrl), or in combination with: compound with no activity (4-(1-(2',5'-dimethoxy-[1,1'-biphenyl]-4-yl)-1H-1,2,3-triazol-4-yl)-3-fluoropyridine), and compounds 3-(1-(3'-methoxy-[1,1'-biphenyl]-4-yl)-1H-1,2,3-triazol-4-yl)benzoic acid, 3-(1-(4-(2,3-dihydrobenzo[b][1,4]dioxin-6-yl)phenyl)-1H-1,2,3-triazol-4-yl)benzoic acid and 3-(1-(2',3'-dimethoxy-[1,1'-biphenyl]-4-yl)-1H-1,2,3-triazol-4-yl)benzoic acid that negatively regulate SOCE. Calcium responses are expressed as changes in fluorescence intensity before and after the addition of selected modulators.

(B) Hek cells were assayed for a calcium response to different concentrations of 3-(1-(2',3'-dimethoxy-[1,1'-biphenyl]-4-yl)-1H-1,2,3-triazol-4-yl)benzoic acid and 3-(1-(4-(2,3-dihydrobenzo[b][1,4]dioxin-6-yl)phenyl)-1H-1,2,3-triazol-4-yl)benzoic acid) (0.1-0.3-1-3-10-30-100 μM) using Fura-2 AM assay. Concentration-response curves represent the AUC % of both compounds as compared to positive control.

Figure 3:
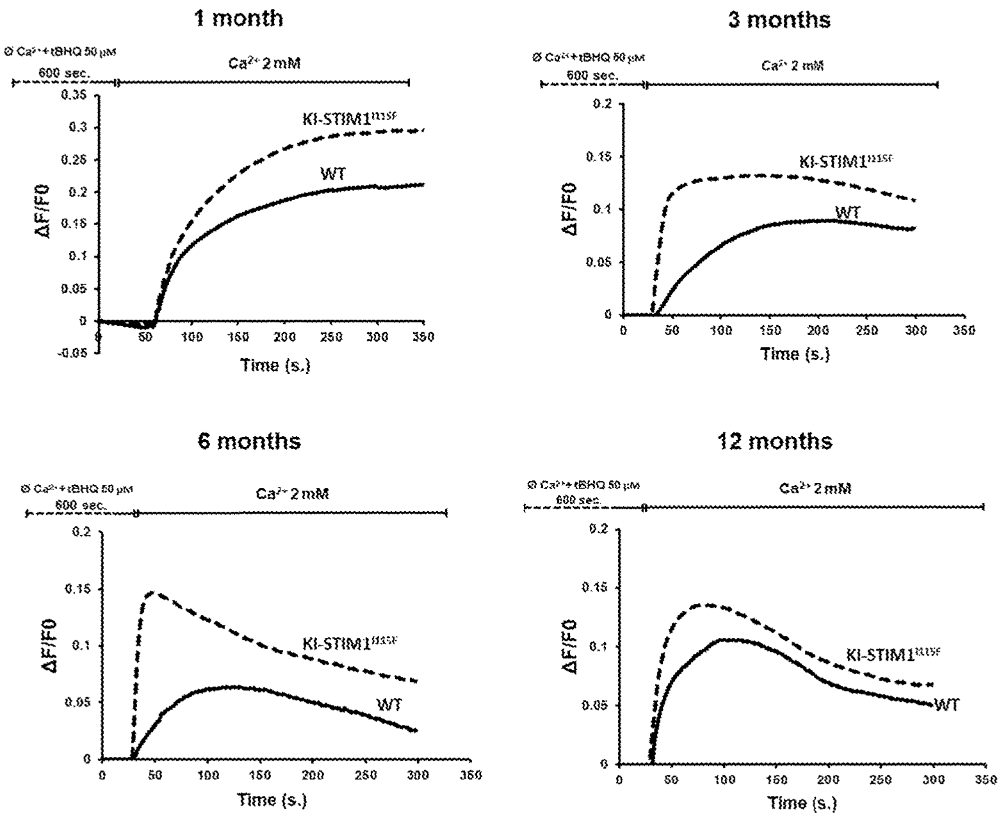

FIG. 3: SOCE is potentiated in myotubes from KI-STIM1$^{I115F}$ mice

SOCE induced by tBHQ in myotubes from wild-type (WT) or KI-STIM1$^{I115F}$ mice. Traces are the average of at least 180 myotubes from 6 plates on two different experimental days. At all-time points, myotubes from 4 animals (2 males, 2 females) for each condition were used.

Figure 4:
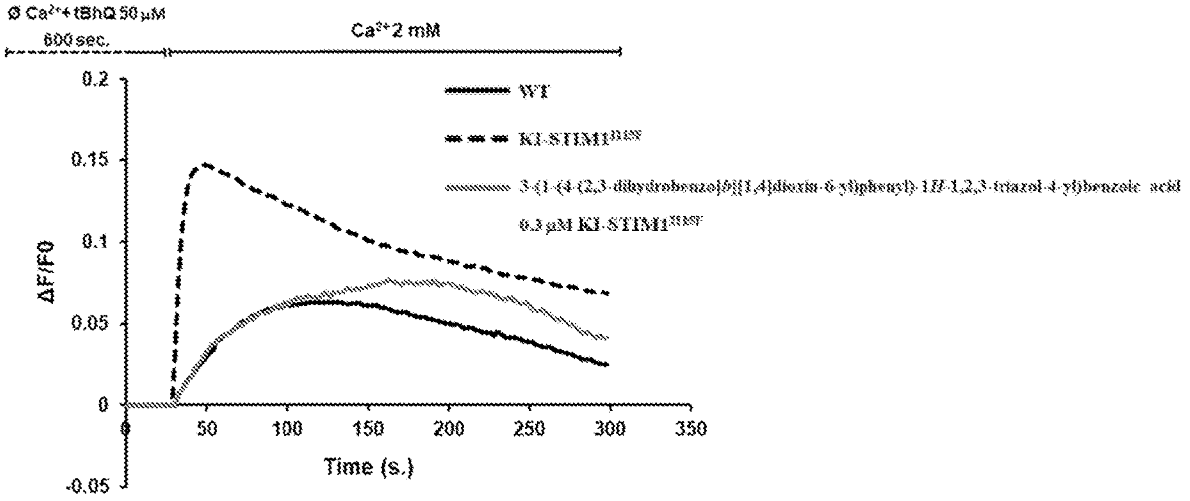

FIG. 4: Evaluation of 3-(1-(3'-methoxy-[1,1'-biphenyl]-4-yl)-1H-1,2,3-triazol-4-yl)benzoic acid effects in myotubes from KI-STIM1$^{I115F}$ mice 3-(1-(3'-Methoxy-[1,1'-biphenyl]-4-yl)-1H-1,2,3-triazol-4-yl)benzoic acid (10 μM) impairs SOCE in myotubes from KI-STIM1$^{I115F}$ mice. In detail, the compound is able to revert the over-activation of STIM1 mutated protein. Traces are the average of at least 180 myotubes from 6 plates on two different experimental days.

Figure 5:
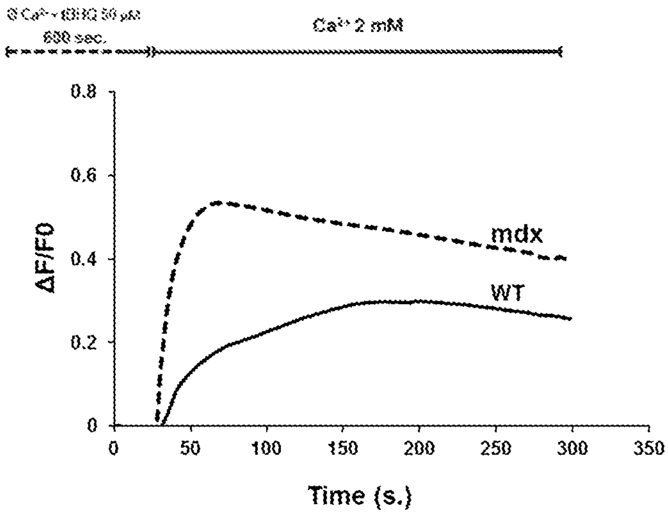

FIG. 5: SOCE is potentiated in myotubes from mdx mice.

SOCE induced by tBHQ in myotubes from wild-type (WT) or mdx mice. Traces are the average of at least 180 myotubes from 6 plates on two different experimental days. At all-time points, myotubes from 4 animals (2 males, 2 females) for each condition were used.

Figure 6:
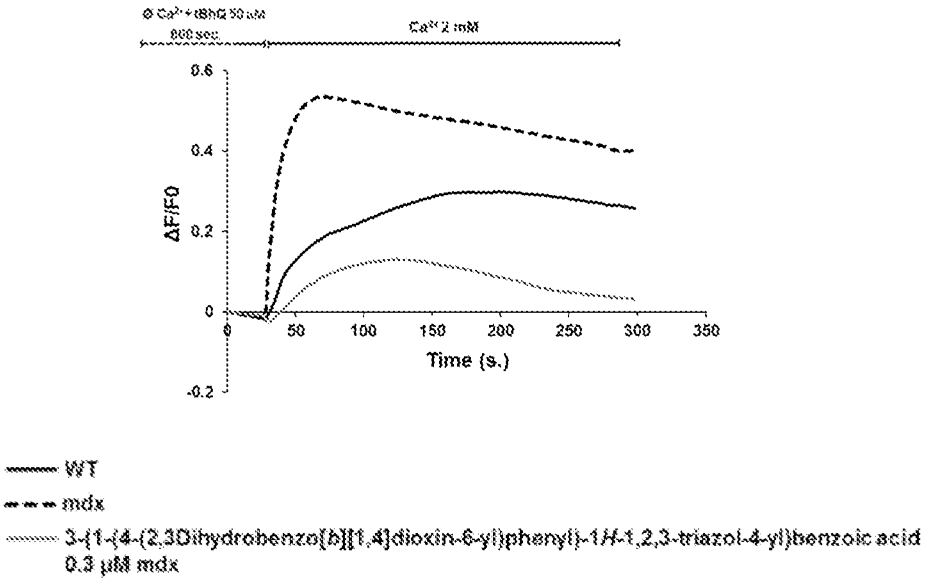

FIG. 6: Evaluation of 3-(1-(4-(2,3-Dihydrobenzo[b][1,4]dioxin-6-yl)phenyl)-1H-1,2,3-triazol-4-yl)benzoic acid effects in myotubes from mdx mice.

3-(1-(3'-Methoxy-[1,1'-biphenyl]-4-yl)-1H-1,2,3-triazol-4-yl)benzoic acid (10 μM) impairs SOCE in myotubes from mdx mice. In detail, the compound is able to revert the over-activation of DMD mutated protein. Traces are the average of at least 180 myotubes from 6 plates on two different experimental days.

Figure 7:
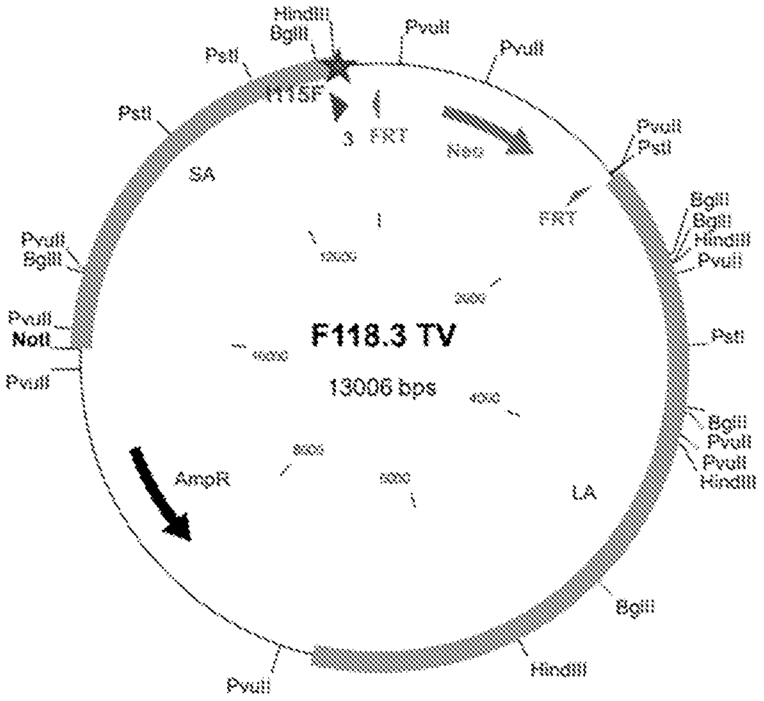

FIG. 7: The targeting vector F118.3 TV.

The base exchanged (indicated by a star) in exon 3 of Stim1 (indicated by an arrow head) is inserted together with the FRT-flanked neomycin resistance cassette. The long arm of homology has a length of 5.3 kb whereas the short arm of homology extends for 2.8 kb (LA and SA; indicated by boxes). Restriction enzymes used for confirmation are indicated. The targeting vector can be linearized with NotI prior to the electroporation.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The term "alkyl" as used herein refers to a monovalent straight or branched chain group derived from an unsaturated hydrocarbon of one to eight carbons. The alkyl groups of this invention can be optionally substituted.

The term "alkenyl" as used herein refers to a monovalent straight or branched chain group derived from a hydrocarbon of two to eight carbons having at least one carbon-carbon double bond. The alkenyl groups of this invention can be optionally substituted.

The term "alkynyl" as used herein refers to a monovalent straight or branched chain group derived from a hydrocarbon of two to eight carbons having at least one carbon-carbon triple bond. The alkynyl groups of this invention can be optionally substituted.

The term "aryl" as used herein refers to a mono- or bicyclic carbocyclic ring system having at least one aromatic ring that can be optionally substituted. The aryl group can be fused to a cyclohexane, cyclohexene, cyclopentane or cyclopentene ring in which case the aryl group can be attached through the ring to which it is attached or through the aromatic ring itself. The aryl groups of this invention can be optionally substituted.

The term "heteroaryl" as used herein refers to an aryl group as defined above containing one, two, three or four heteroatoms independently selected from the group consisting of nitrogen, oxygen and sulfur. Preferably, the heteroaryl group is represented by benzimidazolyl, benzofuryl, benzothiazolyl, benzothienyl, benzoxazolyl, furyl, imidazolinyl, imidazolyl, indolyl, isoquinolyl, isothiazolidinyl, isothiazolyl, isoxazolyl, oxadiazolyl, oxazolidinyl, oxazolyl, pyrazolidinyl, pyrazinyl, pyrazolyl, pyrazolinyl, pyridazinyl, pyridyl, pyrimidinyl, pyrimidyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, triazolyl, and the like. More preferably, the heteroaryl group is represented by nitrogen-containing heterocycles such as pyridyl, triazolyl and the like.

The term "cycloalkyl" as used herein refers to a monovalent saturated cyclic or bicyclic hydrocarbon of three to six carbons. The cycloalkyl groups of this invention can be optionally substituted.

The term "halogen" as used herein refers to F, Cl, Br, or I.

The term "heterocyclic" as used herein refers to a 4-, 5-, 6- or 7-membered ring containing one, two or three heteroatoms independently selected from the group consisting of nitrogen, oxygen and sulfur. The 4- and 5-membered rings have 0, 1, or 2 double bonds and the 6- and 7-membrered rings have 0, 1, 2, or 3 double bonds. The nitrogen and sulfur atoms can be optionally oxidized, and the nitrogen atom can be optionally quaternized. The term "heterocyclic" also includes bicyclic, tricyclic, and tetracyclic groups in which a heterocyclic ring is fused to one or two rings selected from an aryl ring, a cyclohexane ring, a cyclohexene ring, a cyclopentane ring, a cyclopentene ring or another monocyclic heterocyclic ring. Heterocycles of this type can be attached through the ring to which they are fused or through the heterocyclic ring itself. Heterocycles include, but are not limited to, acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, dioxanyl, dioxolanyl, furyl, homopiperidinyl, imidazolidinyl, imidazolinyl, imidazolyl, indolyl, isoquinolyl, isothiazolidinyl, isothiazolyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like. The heterocycle groups of this invention can be optionally substituted. Preferably, the heterocyclic group is selected from nitrogen-containing heterocycles such as pyridyl, triazolyl, and oxygen-containing heterocycles, such as dioxanyl and dioxolanyl.

The term "pharmaceutically acceptable salt" as used herein refers to those salts which are, within the scope of sound medical judgement, suitable for use in contact with the tissues of humans and lower animals without undue toxicity, irritation, allergic response and the like and are commensurate with a reasonable benefit/risk ratio.

The term "pharmaceutically acceptable hydrate and/or solvate" as used herein refers to a crystal form of a substance which contains one or more water and/or solvent molecules.

In an embodiment the present disclosure provides a compound of formula (I):

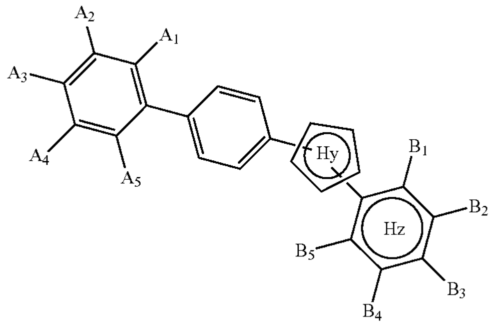

(I)

wherein ring Hy is selected from

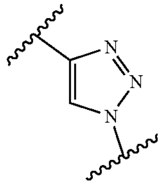

and

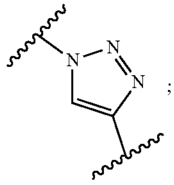

;

ring Hz is selected from an aryl or heteroaryl group;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHCOR_1$, $NHSO_2R_1$, $CONHR_1$, $CONR_1R_2$, $SO_2NHR_1$, COOH, $COOR_1$, $NO_2$, CN, a 5-6 membered O-heterocyclic group;

$A_1$ and $A_2$, or $A_2$ and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are identical or different and independently selected from H, $CH_2COOH$, COOH, $COOR_3$, CN, $CF_3$, Br, I, Cl, F, 1H-tetrazol-5-yl;

$R_1$ and $R_2$ are identical or different from each other and independently selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;

$R_3$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$-$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heteroaryl, wherein m is an integer 1 to 4;

pharmaceutically acceptable hydrates and/or solvates and/or salts thereof, with the exception of: 4'-(4-phenyl-1H-1,2,3-triazol-1-yl)-[1,1'-biphenyl]-4-carbonitrile; 1-(4'-methoxy-[1,1'-biphenyl]-4-yl)-4-phenyl-1H-1,2, 3-triazole; 2-(4-(4-phenyl-1H-1,2,3-triazol-1-yl)phenyl)pyridine; 1-(2'-ethoxy-4'-fluoro-[1,1'-biphenyl]-4-yl)-4-phenyl-1H-1,2,3-triazole; 2-fluoro-5-(4-(4-phenyl-1H-1,2,3-triazol-1-yl)phenyl)pyridine; 1-(3'-(methylsulfonyl)-[1,1'-biphenyl]-4-yl)-4-phenyl-1H-1,2,3-triazole; 5-(4-(4-phenyl-1H-1,2,3-triazol-1-yl)phenyl)nicotinonitrile; 1-(2'-chloro-[1,1'-biphenyl]-4-yl)-4-phenyl-1H-1,2,3-triazole; 1-(5'-chloro-2'-fluoro-[1,1'-biphenyl]-4-yl)-4-phenyl-1H-1,2,3-triazole; 1-(5'-fluoro-2'-methoxy-[1,1'-biphenyl]-4-yl)-4-phenyl-1H-1,2,3-triazole; 1-([1,1'-biphenyl]-4-yl)-4-phenyl-1H-1,2,3-triazole; 4'-(4-(pyridin-2-yl)-1H-1,2,3-triazol-1-yl)-[1,1'-biphenyl]-4-amine; 4'-(4-(pyridin-2-yl)-1H-1,2,3-triazol-1-yl)-[1,1'-biphenyl]-4-ol; N-(4'-(4-phenyl-1H-1,2,3-triazol-1-yl)-[1,1'-biphenyl]-2-yl)-2-(trifluoromethyl)benzamide; N-(5-fluoro-4'-(4-phenyl-1H-1,2,3-triazol-1-yl)-[1,1'-biphenyl]-2-yl)-2-(trifluoromethyl)benzamide; 4-[4-(4-biphenyl-1H-1,2,3-triazol-1-yl]pyridine-2,6-dicarboxylic acid.

In one or more embodiments, when $R_1$, $R_2$ and $R_3$, if present, are independently selected from substituted $C_{1-8}$ alkyl group, substituted $C_{2-8}$ alkenyl group, substituted $C_{2-8}$ alkynyl group, substituted $C_{3-6}$ cycloalkyl, substituted aryl, substituted heterocyclic group, the one or more substituents are independently selected from halogen, $CH_3$, $CH_2F$, $CHF_2$, $CF_3$, $OR_2$, CN, $COOR_4$, $CONR_4R_5$, $NR_4R_5$, $NHCOR_4$, $NHSO_2R_4$, $S(O)R_4$, $S(O)_2R_4$, and $SO_2NHR_4$, wherein $R_4$ and $R_5$ are the same or different and independently selected from H, $C_1$-$C_8$ alkyl group unsubstituted or substituted with one or more halogen atoms, and $C_3$-$C_6$ cycloalkyl group unsubstituted or substituted with one or more halogen atoms.

In one or more preferred embodiments, $R_1$, $R_2$ and $R_3$ are selected from unsubstituted methyl, ethyl, tert-butyl, isopropyl, phenyl and benzyl.

In one or more preferred embodiments, ring Hz is selected from

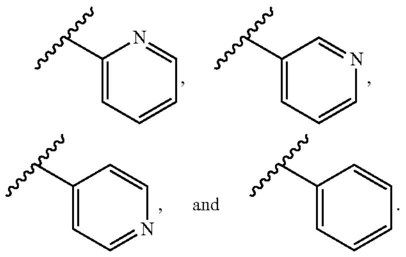
, , and .

In one or more preferred embodiments, $A_1$ substituent is selected from H, F, OMe, a 5-6 membered O-heterocyclic group.

In one or more preferred embodiments, $A_2$ substituent is selected from H, OMe, SMe, OH, a 5-6 membered O-heterocyclic group.

In one or more preferred embodiments, $A_3$ substituent is selected from H, OMe, a 5-6 membered O-heterocyclic group.

In one or more preferred embodiments, $A_4$ substituent is selected from H, OMe, a 5-6 membered O-heterocyclic group.

In one or more preferred embodiments, $A_5$ substituent is selected from H, OMe a 5-6 membered O-heterocyclic group.

In one or more preferred embodiments, two adjacent groups at position $A_1$, $A_2$, $A_3$, $A_4$ or $A_5$ form a 5-6 member O-heterocyclic group fused with the phenyl ring to which they are attached, the heterocyclic group fused with the phenyl ring being selected from dihydrobenzodioxinyl or benzodioxolyl.

In one or more preferred embodiments, $B_1$ substituent is selected from H and F.

In one or more preferred embodiments, $B_2$ substituent is selected from H, $CH_2COOH$, COOH, COOMe, CN, and 1H-tetrazol-5-yl.

In one or more preferred embodiments, $B_3$ is H.

In one or more preferred embodiments, $B_4$ substituent is selected from H, $CH_2COOH$, COOH, COOMe, CN, and 1H-tetrazol-5-yl.

In one or more preferred embodiments, $B_5$ substituent is selected from H and F.

Compared to the compounds described in the present invention, Synta66 exhibits a considerable cytotoxicity at 10 μM, with a residual cell viability of 76% after 24 hours. Under the same conditions, the described biphenyl 1,4-disubstituted 1,2,3-triazol SOCE modulators are not cytotoxic, with a cell viability higher than 90% after 24 hours. Moreover, the biphenyl modulators maintain a potency comparable to Synta66 in inhibiting SOCE activity with $IC_{50}$ values in the nanomolar range in both cases.

In an embodiment, the present description concerns compounds of formula (I) for use as a medicament and pharmaceutical compositions comprising the same (I)

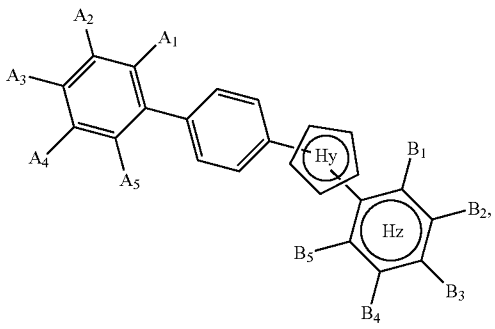

wherein the residues $A_1$, $A_2$, $A_3$, $A_4$, $A_5$, $B_1$, $B_2$, $B_3$, $B_4$, $B_5$, Hy, and Hz have the meanings set forth above, with the exception of: 1-(2'-ethoxy-4'-fluoro-[1,1'-biphenyl]-4-yl)-4-phenyl-1H-1,2,3-triazole; 2-fluoro-5-(4-(4-phenyl-1H-1,2,3-triazol-1-yl)phenyl)pyridine; 1-(3'-(methylsulfonyl)-[1,1'-biphenyl]-4-yl)-4-phenyl-1H-1,2,3-triazole; 5-(4-(4-phenyl-1H-1,2,3-triazol-1-yl)phenyl)nicotinonitrile; 1-(2'-chloro-[1,1'-biphenyl]-4-yl)-4-phenyl-1H-1,2,3-triazole; 1-(5'-chloro-2'-fluoro-[1,1'-biphenyl]-4-yl)-4-phenyl-1H-1,2,3-triazole; 1-(5'-fluoro-2'-methoxy-[1,1'-biphenyl]-4-yl)-4-phenyl-1H-1,2,3-triazole; 1-([1,1'-biphenyl]-4-yl)-4-phenyl-1H-1,2,3-triazole.

In an embodiment, the present description concerns compounds of formula (I) for use in the treatment of disease condition depending on increased/decreased activity of SOCE

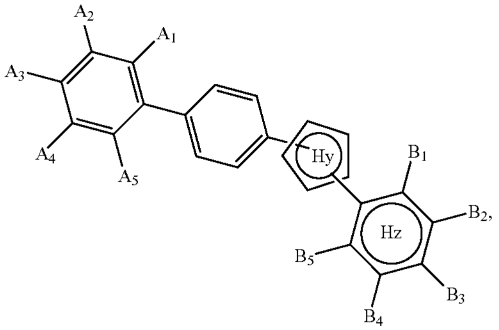

(I)

wherein the residues $A_1$, $A_2$, $A_3$, $A_4$, $A_5$, $B_1$, $B_2$, $B_3$, $B_4$, $B_5$, Hy, and Hz have the meanings set forth above.

Accordingly, the compounds of formula (I) are useful for the prevention or treatment of:

- Diseases linked to loss- or gain-of-function STIM1/Orai 1 mutations, including but not limited to, immunodeficiencies (T-cell immunodeficiency, lymphoproliferative diseases, autoimmunity, congenital myopathy, anhydrosis, dental enamel, and an impairment in thrombus formation due to a defect in platelet activation), tubular aggregate myopathy (TAM), Stormorken syndrome and York platelet syndrome.
- Muscular dystrophies, including Duchenne muscular dystrophy;
- Inflammatory diseases, including mild and severe acute pancreatitis, chronic pancreatitis and post-ERCP pancreatitis.

Compounds of formula (I) can be administered in various routes appropriate to the condition to be treated. Suitable routes include oral, parenteral (including subcutaneous, intramuscular, intravenous, intra-arterial, intradermal, intrathecal and epidural), transdermal, rectal, nasal, topical (including buccal and sublingual), vaginal, intraperitoneal, intrapulmonary and intranasal.

Compounds of formula (I) can be formulated as a pharmaceutical composition in the form of tablet, capsule, aqueous solution, granule, powder, suspension, cream, syrup, gel, emulsion, and the like.

The dosage depends on a variety of factors including the age, weight and condition of the patient and the route of administration. Although daily dosage can vary from one individual to another, the compound/s will be administered to an adult human in a range of 0.0001-50 mg/kg of body weight as daily single dose or 0.01 to 1 mg/kg as daily repeated doses.

Tablets contain the compound/s of formula (I) in a mixture with non-toxic pharmaceutically excipients suitable for the manufacture of tablets. Exemplary excipients could be: inert diluents, such as sodium carbonate, lactose, dextrose, cellulose etc.; granulating and disintegrating agents as maize starch, glycolate, alginic acid; binding agents as gelatin or acacia; lubricating agents, for example silica magnesium or calcium stearate, stearic acid or talc. For preparing suppositories, a mixture of for example fatty acid glycerides or cocoa butter is first melted and the compound/s of formula (I) is/are dissolved homogenously by stirring. The homogenous mixture is then cooled into convenient sized molds. Liquid preparations, which include solutions, suspensions and emulsions, contain the formula (I) compound/s in a mixture of excipients suitable for the manufacture of aqueous suspension such as sodium carboxymethylcellulose, methylcellulose, resin, sodium alginate and natural or synthetic gums. Eventually the liquid preparation may contain suitable colorants, flavors, stabilizers, preservatives and thickening agents as desired.

Compounds of the present invention may also be co-administered with one or more additional therapeutic agents. In a preferred embodiment, said additional therapeutic agents, include, but are not limited to, non-steroidal anti-inflammatory drugs (such as indomethacin) and steroidal anti-inflammatory drugs.

Moreover, more than one compound according to formula (I) can be co-administered.

Compounds of formula (I) include, but are not limited to, the compounds shown in Table 1.

TABLE 1

| Compound name and (number) | Structure |
|---|---|
| 3-(1-([1,1'-Biphenyl]-4-yl)-1H-1,2,3-triazol-4-yl)benzoic acid (10) | 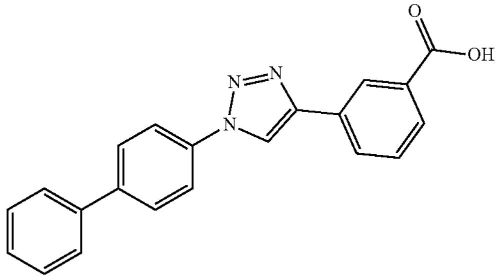 [SMILES: O=C(O)c1cccc(-c2cn(-c3ccc(-c4ccccc4)cc3)nn2)c1] |

TABLE 1-continued
| Compound name and (number) | Structure |
| --- | --- |
| 3-(1-(3'-(Methylthio)-[1,1'-biphenyl]-4-yl)-1H-1,2,3-triazol-4-yl)benzoic acid (11) | 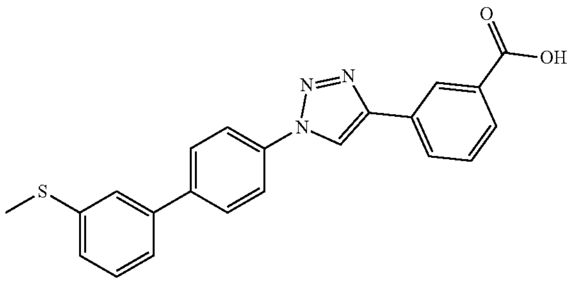 [SMILES: CSc1cccc(-c2ccc(-n3cc(-c4cccc(C(=O)O)c4)nn3)cc2)c1] |
| 3-(1-(2'-Methoxy-[1,1'-biphenyl]-4-yl)-1H-1,2,3-triazol-4-yl)benzoic acid (12) | 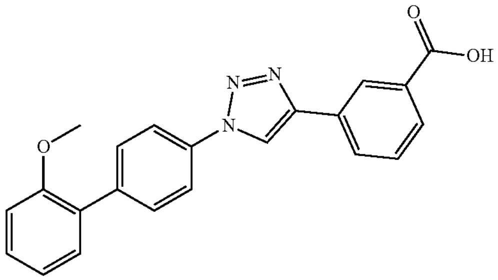 [SMILES: COc1ccccc1-c1ccc(-n2cc(-c3cccc(C(=O)O)c3)nn2)cc1] |
| 3-(1-(3'-Methoxy-[1,1'-biphenyl]-4-yl)-1H-1,2,3-triazol-4-yl)benzoic acid (13) | 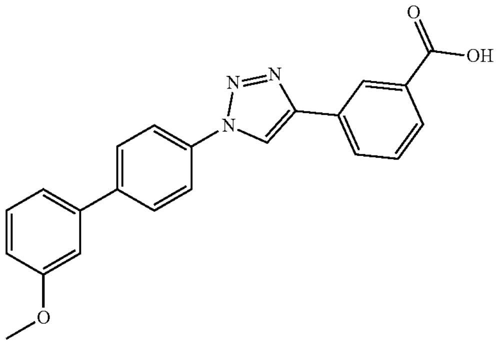 [SMILES: COc1cccc(-c2ccc(-n3cc(-c4cccc(C(=O)O)c4)nn3)cc2)c1] |
| 3-(1-(3'-Hydroxy-[1,1'-biphenyl]-4-yl)-1H-1,2,3-triazol-4-yl)benzoic acid (14) | 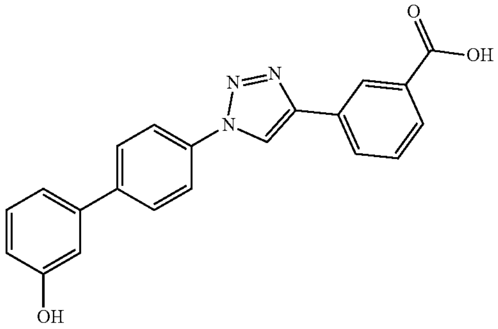 [SMILES: O=C(O)c1cccc(-c2cn(-c3ccc(-c4cccc(O)c4)cc3)nn2)c1] |
| 3-(1-(2',4'-Dimethoxy-[1,1'-biphenyl]-4-yl)-1H-1,2,3-triazol-4-yl)benzoic acid (15) | 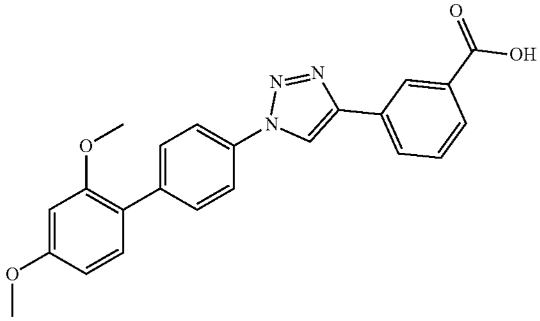 [SMILES: COc1ccc(-c2ccc(-n3cc(-c4cccc(C(=O)O)c4)nn3)cc2)c(OC)c1] |

TABLE 1-continued
| Compound name and (number) | Structure |
| --- | --- |
| 3-(1-(3',5'-Dimethoxy-[1,1'-biphenyl]-4-yl)-1H-1,2,3-triazol-4-yl)benzoic acid (16) | 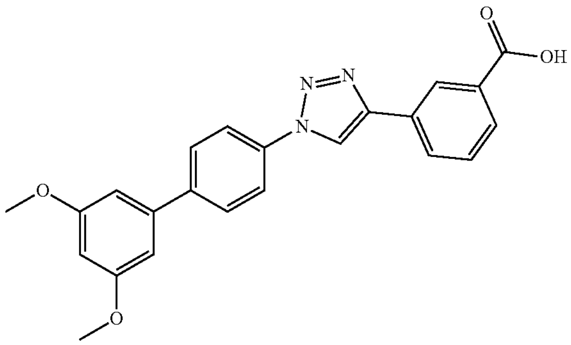 [SMILES: COc1cc(OC)cc(-c2ccc(-n3cc(-c4cccc(C(=O)O)c4)nn3)cc2)c1] |
| 3-(1-(4-(Benzo[d][1,3]dioxol-5-yl)phenyl)-1H-1,2,3-triazol-4-yl)benzoic acid (17) | 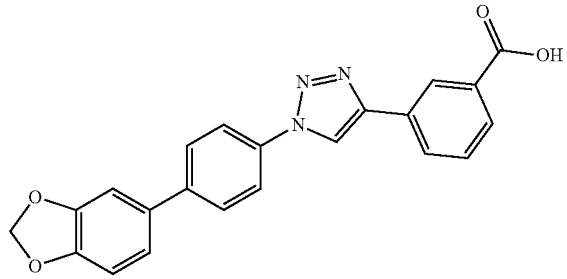 [SMILES: O=C(O)c1cccc(-c2cn(-c3ccc(-c4ccc5c(c4)OCO5)cc3)nn2)c1] |
| 3-(1-(4-(2,3-Dihydrobenzo[b][1,4]dioxin-6-yl)phenyl)-1H-1,2,3-triazol-4-yl)benzoic acid (18) | 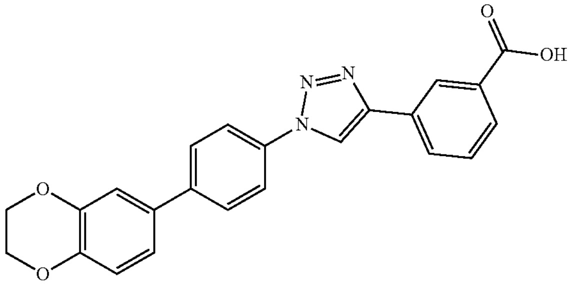 [SMILES: O=C(O)c1cccc(-c2cn(-c3ccc(-c4ccc5c(c4)OCCO5)cc3)nn2)c1] |
| 3-(1-(3',4'-Dimethoxy-[1,1'-biphenyl]-4-yl)-1H-1,2,3-triazol-4-yl)benzoic acid (19) | 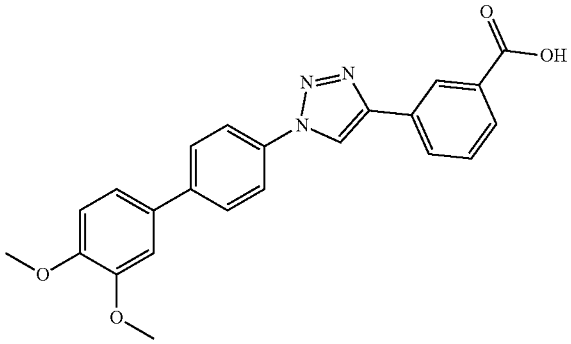 [SMILES: COc1ccc(-c2ccc(-n3cc(-c4cccc(C(=O)O)c4)nn3)cc2)cc1OC] |

TABLE 1-continued
| Compound name and (number) | Structure |
| --- | --- |
| 3-(1-(2',3'-Dimethoxy-[1,1'-biphenyl]-4-yl)-1H-1,2,3-triazol-4-yl)benzoic acid (20) | 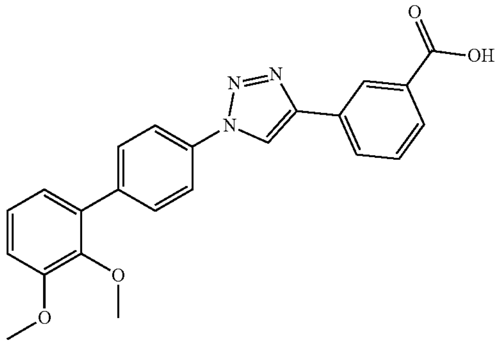 [SMILES: COc1cccc(-c2ccc(-n3cc(-c4cccc(C(=O)O)c4)nn3)cc2)c1OC] |
| 3-(1-(4-(2,3-Dihydrobenzo[b][1,4]dioxin-5-yl)phenyl)-1H-1,2,3-triazol-4-yl)benzoic acid (21) | 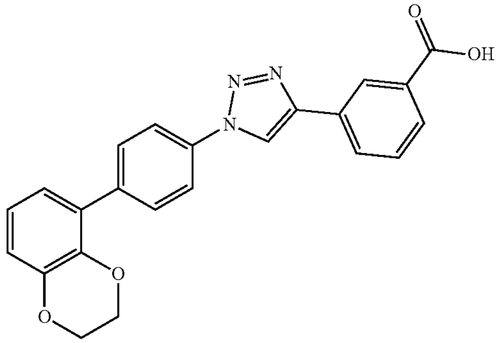 [SMILES: O=C(O)c1cccc(-c2cn(-c3ccc(-c4cccc5c4OCCO5)cc3)nn2)c1] |
| 3-(1-(2',6'-Dimethoxy-[1,1'-biphenyl]-4-yl)-1H-1,2,3-triazol-4-yl)benzoic acid (22) | 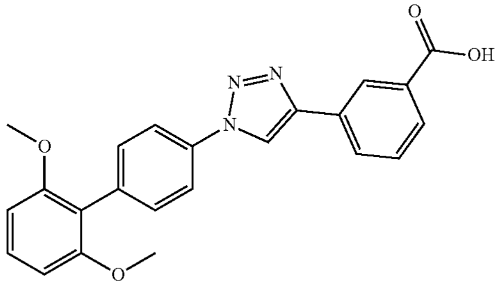 [SMILES: COc1cccc(OC)c1-c1ccc(-n2cc(-c3cccc(C(=O)O)c3)nn2)cc1] |
| 3-(1-(2'-Fluoro-5'-methoxy-[1,1'-biphenyl]-4-yl)-1H-1,2,3-triazol-4-yl)benzoic acid (23) | 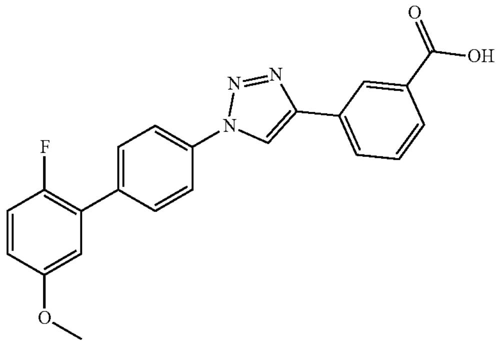 [SMILES: COc1ccc(F)c(-c2ccc(-n3cc(-c4cccc(C(=O)O)c4)nn3)cc2)c1] |

TABLE 1-continued
| Compound name and (number) | Structure |
|---|---|
| 3-(1-(2',5'-Dimethoxy-[1,1'-biphenyl]-4-yl)-1H-1,2,3-triazol-4-yl)benzoic acid (24) | 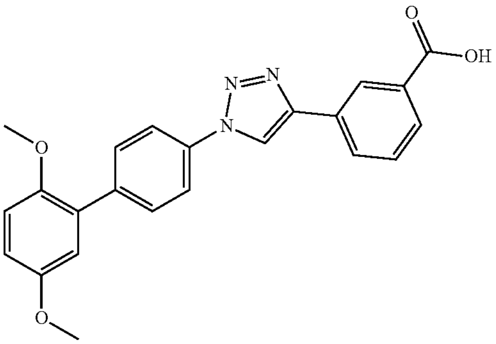 [SMILES: COc1ccc(OC)c(-c2ccc(-n3cc(-c4cccc(C(=O)O)c4)nn3)cc2)c1] |
| 4-(1-(2',5'-Dimethoxy-[1,1'-biphenyl]-4-yl)-1H-1,2,3-triazol-4-yl)picolinic acid (25) | 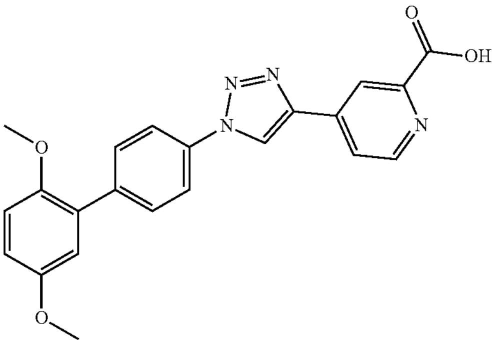 [SMILES: COc1ccc(OC)c(-c2ccc(-n3cc(-c4ccnc(C(=O)O)c4)nn3)cc2)c1] |
| 4-(1-(2',5'-Dimethoxy-[1,1'-biphenyl]-4-yl)-1H-1,2,3-triazol-4-yl)-3-fluoropyridine (26) | 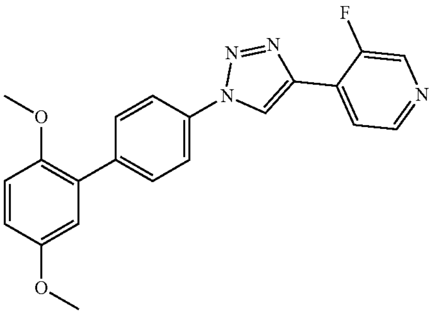 [SMILES: COc1ccc(OC)c(-c2ccc(-n3cc(-c4ccncc4F)nn3)cc2)c1] |
| 4-(1-(2',5'-Dimethoxy-[1,1'-biphenyl]-4-yl)-1H-1,2,3-triazol-4-yl)pyridine (27) | 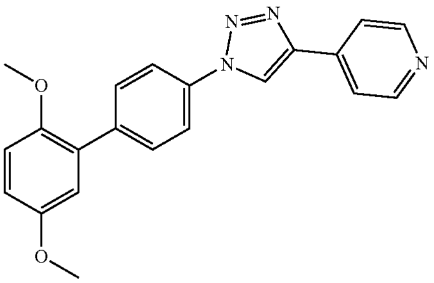 [SMILES: COc1ccc(OC)c(-c2ccc(-n3cc(-c4ccncc4)nn3)cc2)c1] |
| 3-(1-(2',5'-Dimethoxy-[1,1'-biphenyl]-4-yl)-1H-1,2,3-triazol-4-yl)pyridine (28) | 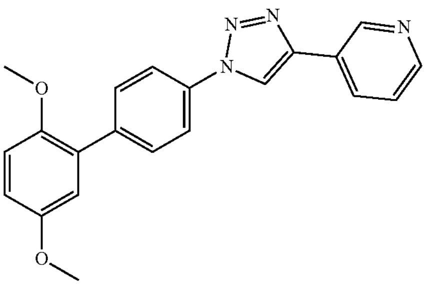 [SMILES: COc1ccc(OC)c(-c2ccc(-n3cc(-c4cccnc4)nn3)cc2)c1] |

TABLE 1-continued
| Compound name and (number) | Structure |
|---|---|
| 2-(1-(2',5'-Dimethoxy-[1,1'-biphenyl]-4-yl)-1H-1,2,3-triazol-4-yl)pyridine (29) | 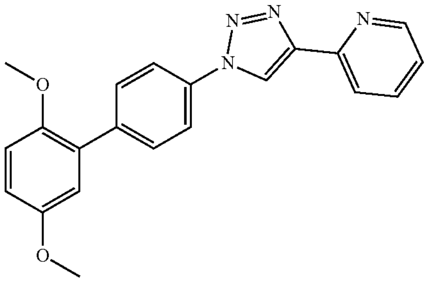 [SMILES: COc1ccc(OC)c(-c2ccc(-n3cc(-c4ccccn4)nn3)cc2)c1] |
| 3-(1-(4-(2,3-Dihydrobenzo[b][1,4]dioxin-6-yl)phenyl)-1H-1,2,3-triazol-4-yl)benzonitrile (30) | 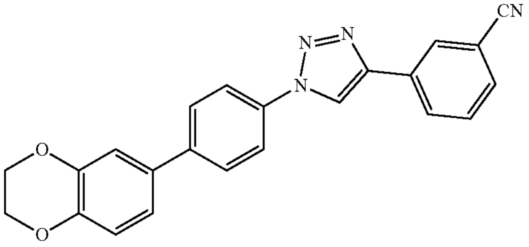 [SMILES: N#Cc1cccc(-c2cn(-c3ccc(-c4ccc5c(c4)OCCO5)cc3)nn2)c1] |
| 5-(3-(1-(4-(2,3-Dihydrobenzo[b][1,4]dioxin-6-yl)phenyl)-1H-1,2,3-triazol-4-yl)phenyl)-1H-tetrazole (31) | 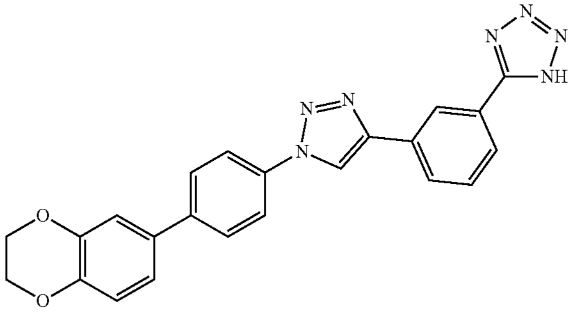 [SMILES: c1cc(-c2cn(-c3ccc(-c4ccc5c(c4)OCCO5)cc3)nn2)cc(-c2nnn[nH]2)c1] |
| 2-(3-(1-(4-(2,3-Dihydrobenzo[b][1,4]dioxin-6-yl)phenyl)-1H-1,2,3-triazol-4-yl)phenyl)acetic acid (32) | 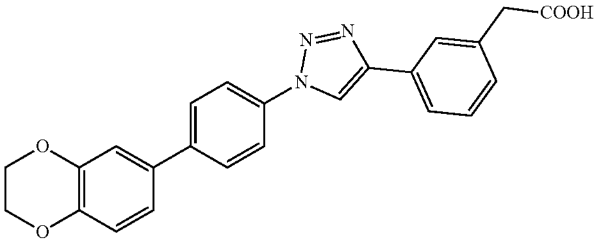 [SMILES: O=C(O)Cc1cccc(-c2cn(-c3ccc(-c4ccc5c(c4)OCCO5)cc3)nn2)c1] |
| 3-(4-([1,1'-Biphenyl]-4-yl)-1H-1,2,3-triazol-1-yl)benzoic acid (33) | 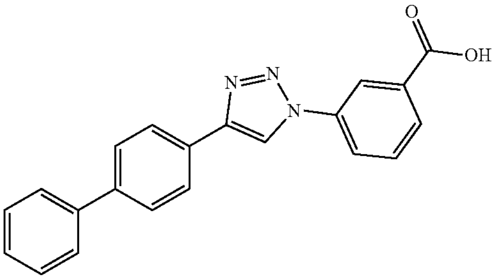 [SMILES: O=C(O)c1cccc(-n2cc(-c3ccc(-c4ccccc4)cc3)nn2)c1] |

TABLE 1-continued
| Compound name and (number) | Structure |
|---|---|
| 3-(4-(3'-(Methylthio)-[1,1'-biphenyl]-4-yl)-1H-1,2,3-triazol-1-yl)benzoic acid (34) | 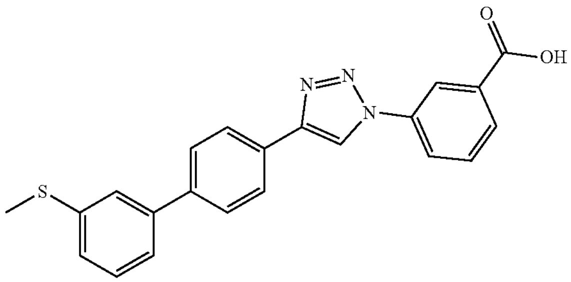 [SMILES: CSc1cccc(-c2ccc(-c3cn(-c4cccc(C(=O)O)c4)nn3)cc2)c1] |
| 3-(4-(2'-Methoxy-[1,1'-biphenyl]-4-yl)-1H-1,2,3-triazol-1-yl)benzoic acid (35) | 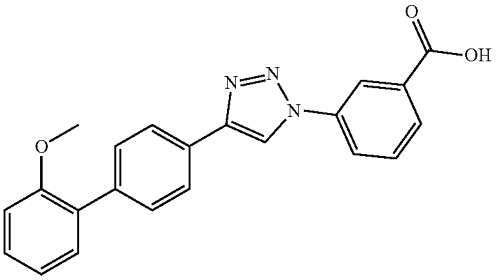 [SMILES: COc1ccccc1-c1ccc(-c2cn(-c3cccc(C(=O)O)c3)nn2)cc1] |
| 3-(4-(3'-Methoxy-[1,1'-biphenyl]-4-yl)-1H-1,2,3-triazol-1-yl)benzoic acid (36) | 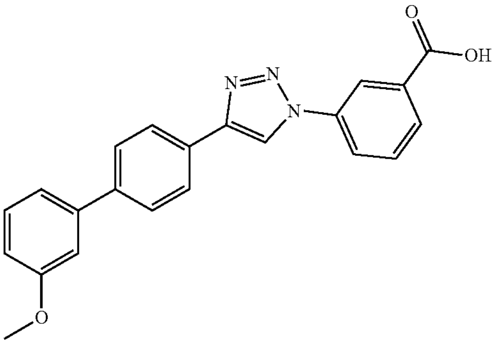 [SMILES: COc1cccc(-c2ccc(-c3cn(-c4cccc(C(=O)O)c4)nn3)cc2)c1] |
| 3-(4-(2',4'-Dimethoxy-[1,1'-biphenyl]-4-yl)-1H-1,2,3-triazol-1-yl)benzoic acid (37) | 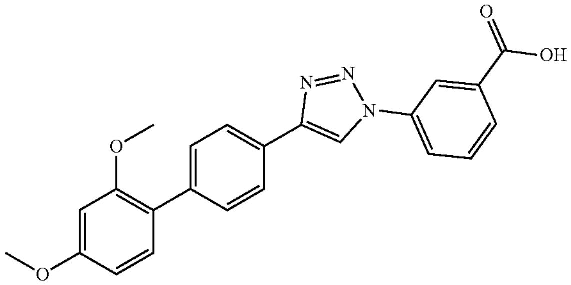 [SMILES: COc1ccc(-c2ccc(-c3cn(-c4cccc(C(=O)O)c4)nn3)cc2)c(OC)c1] |
| 3-(4-(3',5'-Dimethoxy-[1,1'-biphenyl]-4-yl)-1H-1,2,3-triazol-1-yl)benzoic acid (38) | 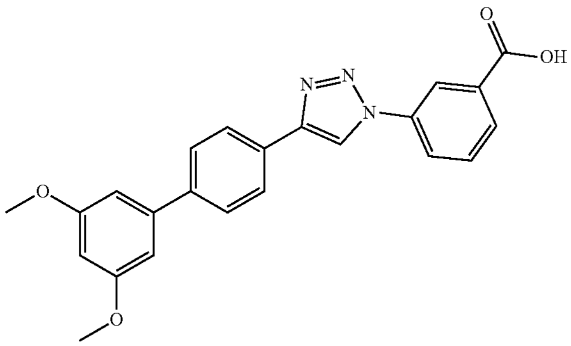 [SMILES: COc1cc(OC)cc(-c2ccc(-c3cn(-c4cccc(C(=O)O)c4)nn3)cc2)c1] |

TABLE 1-continued
| Compound name and (number) | Structure |
|---|---|
| 3-(4-(4-(Benzo[d][1,3]dioxol-5-yl)phenyl)-1H-1,2,3-triazol-1-yl)benzoic acid (39) | 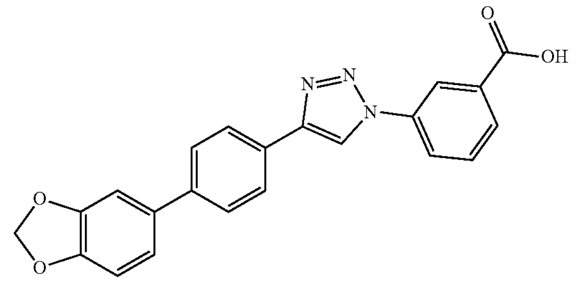 [SMILES: O=C(O)c1cccc(-n2cc(-c3ccc(-c4ccc5c(c4)OCO5)cc3)nn2)c1] |
| 3-(4-(4-(2,3-Dihydrobenzo[b][1,4]dioxin-6-yl)phenyl)-1H-1,2,3-triazol-1-yl)benzoic acid (40) | 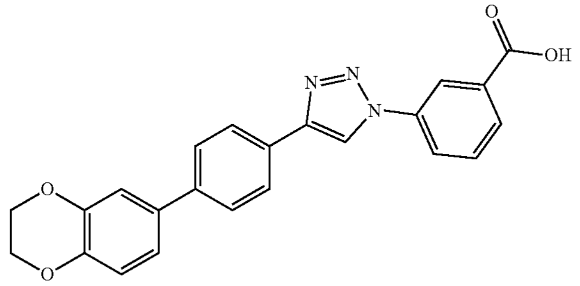 [SMILES: O=C(O)c1cccc(-n2cc(-c3ccc(-c4ccc5c(c4)OCCO5)cc3)nn2)c1] |
| 3-(4-(3',4'-Dimethoxy-[1,1'-biphenyl]-4-yl)-1H-1,2,3-triazol-1-yl)benzoic acid (41) | 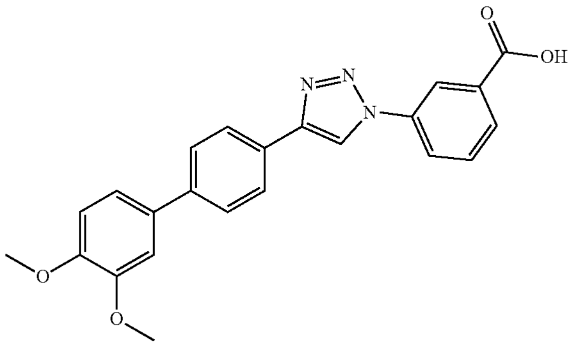 [SMILES: COc1ccc(-c2ccc(-c3cn(-c4cccc(C(=O)O)c4)nn3)cc2)cc1OC] |
| 3-(4-(2',3'-Dimethoxy-[1,1'-biphenyl]-4-yl)-1H-1,2,3-triazol-1-yl)benzoic acid (42) | 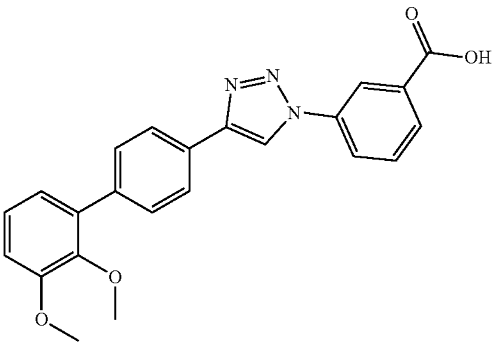 [SMILES: COc1cccc(-c2ccc(-c3cn(-c4cccc(C(=O)O)c4)nn3)cc2)c1OC] |

TABLE 1-continued
| Compound name and (number) | Structure |
| --- | --- |
| 3-(4-(4-(2,3-Dihydrobenzo[b][1,4]dioxin-5-yl)phenyl)-1H-1,2,3-triazol-1-yl)benzoic acid (43) | 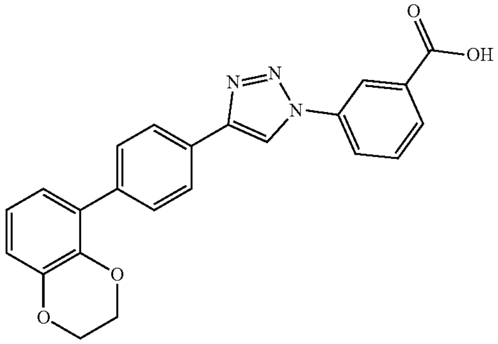 [SMILES: O=C(O)c1cccc(-n2cc(-c3ccc(-c4cccc5c4OCCO5)cc3)nn2)c1] |
| 3-(4-(2',6'-Dimethoxy-[1,1'-biphenyl]-4-yl)-1H-1,2,3-triazol-1-yl)benzoic acid (44) | 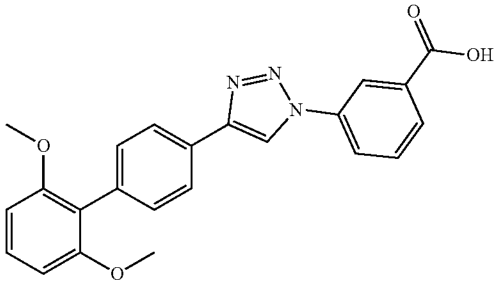 [SMILES: COc1cccc(OC)c1-c1ccc(-c2cn(-c3cccc(C(=O)O)c3)nn2)cc1] |
| 3-(4-(2'-Fluoro-5'-methoxy-[1,1'-biphenyl]-4-yl)-1H-1,2,3-triazol-1-yl)benzoic acid (45) | 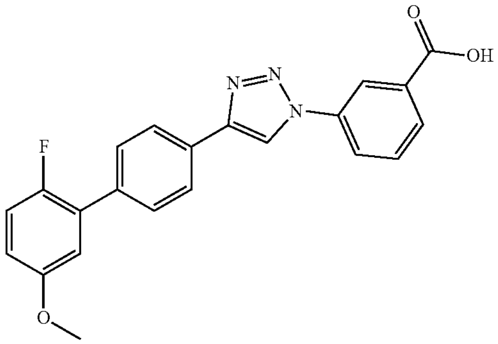 [SMILES: COc1ccc(F)c(-c2ccc(-c3cn(-c4cccc(C(=O)O)c4)nn3)cc2)c1] |
| 3-(4-(2',5'-Dimethoxy-[1,1'-biphenyl]-4-yl)-1H-1,2,3-triazol-1-yl)benzoic acid (46) | 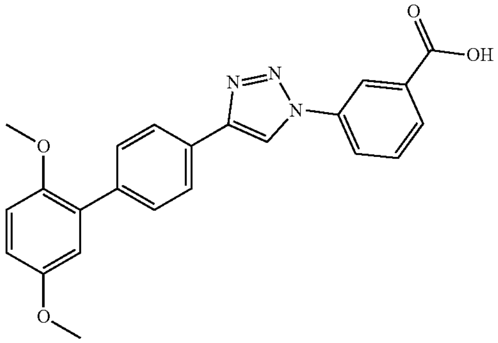 [SMILES: COc1ccc(OC)c(-c2ccc(-c3cn(-c4cccc(C(=O)O)c4)nn3)cc2)c1] |

TABLE 1-continued
| Compound name and (number) | Structure |
| --- | --- |
| Methyl 4-(4-(2',5'-dimethoxy-[1,1'-biphenyl]-4-yl)-1H-1,2,3-triazol-1-yl)picolinate (47) | 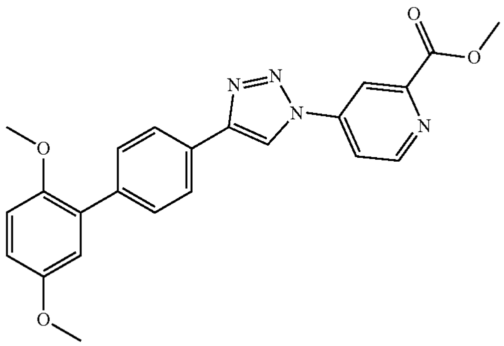 [SMILES: COC(=O)c1cc(-n2cc(-c3ccc(-c4cc(OC)ccc4OC)cc3)nn2)ccn1] |
| 4-(4-(2',5'-Dimethoxy-[1,1'-biphenyl]-4-yl)-1H-1,2,3-triazol-1-yl)picolinic acid (48) | 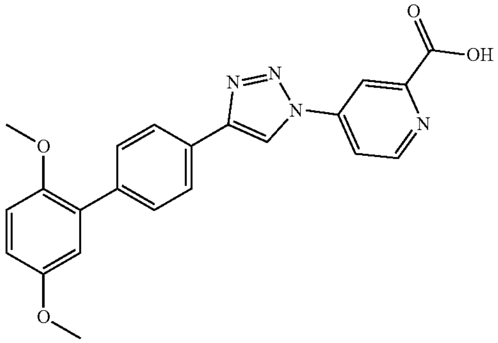 [SMILES: COc1ccc(OC)c(-c2ccc(-c3cn(-c4ccnc(C(=O)O)c4)nn3)cc2)c1] |
| 4-(4-(2',5'-Dimethoxy-[1,1'-biphenyl]-4-yl)-1H-1,2,3-triazol-1-yl)-3-fluoropyridine (49) | 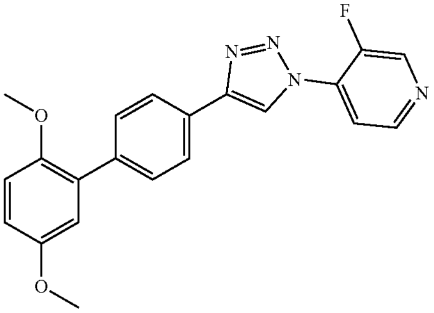 [SMILES: COc1ccc(OC)c(-c2ccc(-c3cn(-c4ccncc4F)nn3)cc2)c1] |
| 4-(4-(2',5'-Dimethoxy-[1,1'-biphenyl]-4-yl)-1H-1,2,3-triazol-1-yl)pyridine (50) | 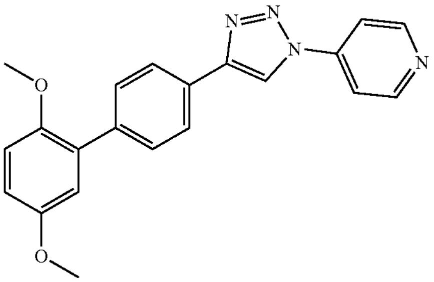 [SMILES: COc1ccc(OC)c(-c2ccc(-c3cn(-c4ccncc4)nn3)cc2)c1] |
| 3-(4-(2',5'-Dimethoxy-[1,1'-biphenyl]-4-yl)-1H-1,2,3-triazol-1-yl)pyridine (51) | 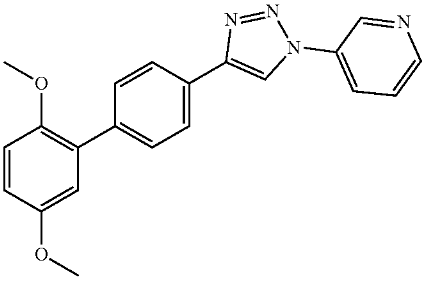 [SMILES: COc1ccc(OC)c(-c2ccc(-c3cn(-c4cccnc4)nn3)cc2)c1] |

General Synthesis of Compounds of Formula (I)

The following schemes show a method for preparing the compounds of formula (I) of the present description. For a more detailed description of the individual reaction steps, see the Examples herein below. Those skilled in the art will appreciate that other synthetic routes may be used to synthesize the compounds of the invention. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of the instant disclosure using conventional chemistry well known to those skilled in the art.

In detail, compounds of formula (IV)

(IV)

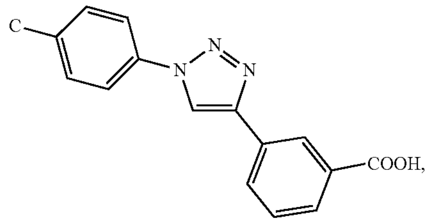

wherein C is selected from 2-methoxyphenyl, 3-methoxyphenyl, phenyl, 3-methylthiophenyl, 2,4-dimethoxyphenyl, 3,5-dimethoxyphenyl, benzo[d][1,3]dioxolyl, dihydrobenzo[b][1,4]dioxinyl, 2,3-dimethoxyphenyl, 2,6-dimethoxyphenyl, 3,4-dimethoxyphenyl, 2-fluoro-5-methoxyphenyl and 3-hydroxyphenyl, can be prepared as outlined in Scheme a below:

Scheme a

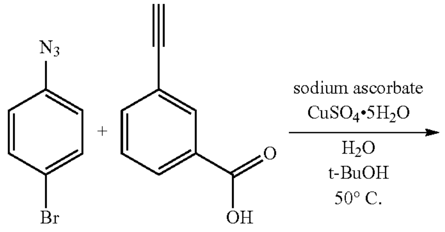

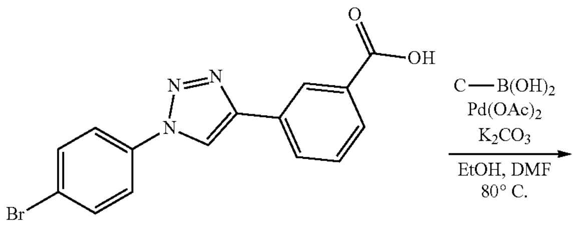

1

-continued

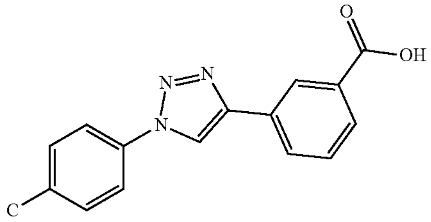

Compounds of Formula IV are synthesized using Suzuki cross-coupling reaction. While boronic acids are commercially available or can be synthesized following synthetic methodologies known in the art, the aryl bromide 1 (intermediate 1) is prepared via the azide-alkyne 1,3-dipolar cycloaddition catalyzed by copper (I) generated in situ by sodium ascorbate. The click reaction between 1-azido-4-bromobenzene and 3-ethynylbenzoic acid gives intermediate 1.

Compounds of formula (V)

(V)

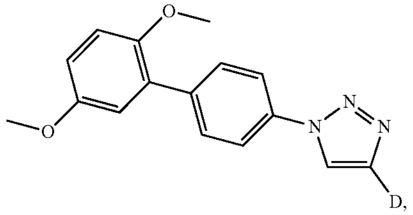

wherein D is selected from pyridin-4-yl, pyridin-3-yl), pyridin-2-yl, 3-fluoropyridin-4-yl, 3-carboxyphenyl, 2-carboxypyridin-4-yl and (2-methoxycarbonyl)pyridin-4-yl, can be prepared as outlined in Scheme b below:

Scheme b

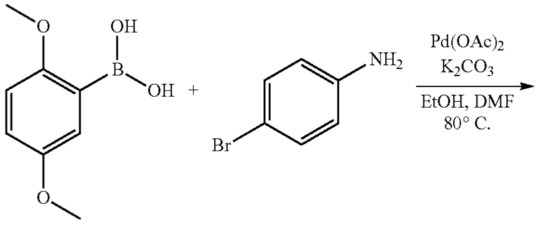

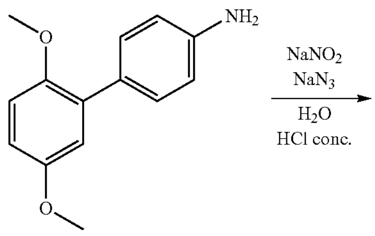

2

-continued

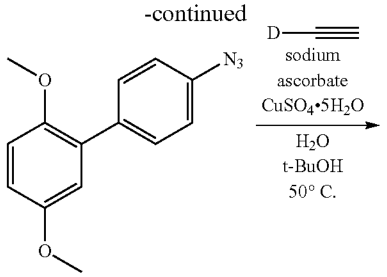

3

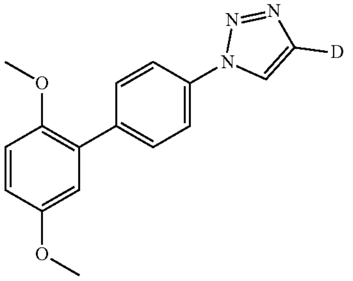

Compounds of Formula V are synthesized via the azide-alkyne 1,3-dipolar cycloaddition catalyzed by copper (I) generated in situ by sodium ascorbate. While alkynes are commercially available or can be synthesized following synthetic methodologies known in the art, the azide 3 is synthesize as depicted in Scheme b. The (2,5-dimethoxyphenyl)boronic acid and the 4-bromoaniline react in a Suzuki cross-coupling reaction to give intermediate 2. Then, diazotization-azidation protocol gives the azide 3 (intermediate 3), that undergoes click chemistry reactions with different alkynes.

Compounds of formula (VI)

(VI)

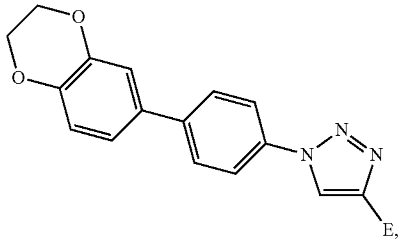

wherein E is selected from (1H-tetrazol-5-yl)phenyl, (carboxymethyl)phenyl and 3-cyanophenyl, can be prepared as outlined in Scheme c below:

Scheme c

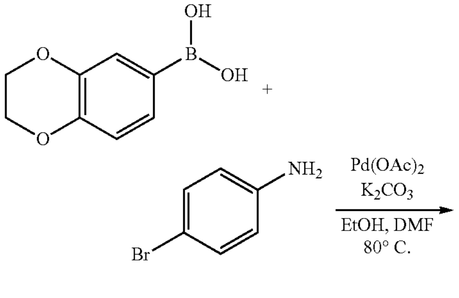

-continued

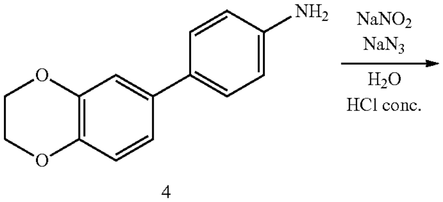

4

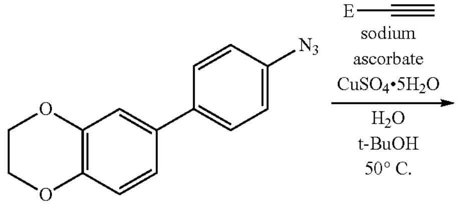

5

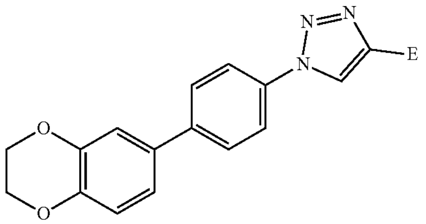

Compounds of Formula VI are synthesized via the azide-alkyne 1,3-dipolar cycloaddition catalyzed by copper (I) generated in situ by sodium ascorbate. While alkynes are commercially available or can be synthesized following synthetic methodologies known in the art, the azide 5 is synthesize as depicted in Scheme c. The (2,3-dihydrobenzo [b][1,4]dioxin-6-yl)boronic acid and the 4-bromoaniline react in a Suzuki cross-coupling reaction to give intermediate 4. Then, diazotation-azidation protocol gives the azide 5 (intermediate 5) that undergoes click chemistry reactions with different alkynes.

Compounds of formula (VII)

(VII)

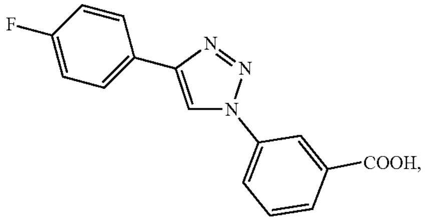

wherein F is selected from 2-methoxyphenyl, 3-methoxyphenyl, phenyl, 3-methylthiophenyl, 2,4-dimethoxyphenyl, 3,5-dimethoxyphenyl, benzo[d][1,3]dioxolyl, dihydrobenzo [b][1,4]dioxinyl, 2,3-dimethoxyphenyl, 2,6-dimethoxyphenyl, 3,4-dimethoxyphenyl, 2-fluoro-5-methoxyphenyl and 3-hydroxyphenyl, can be prepared as outlined in Scheme d below:

Scheme d

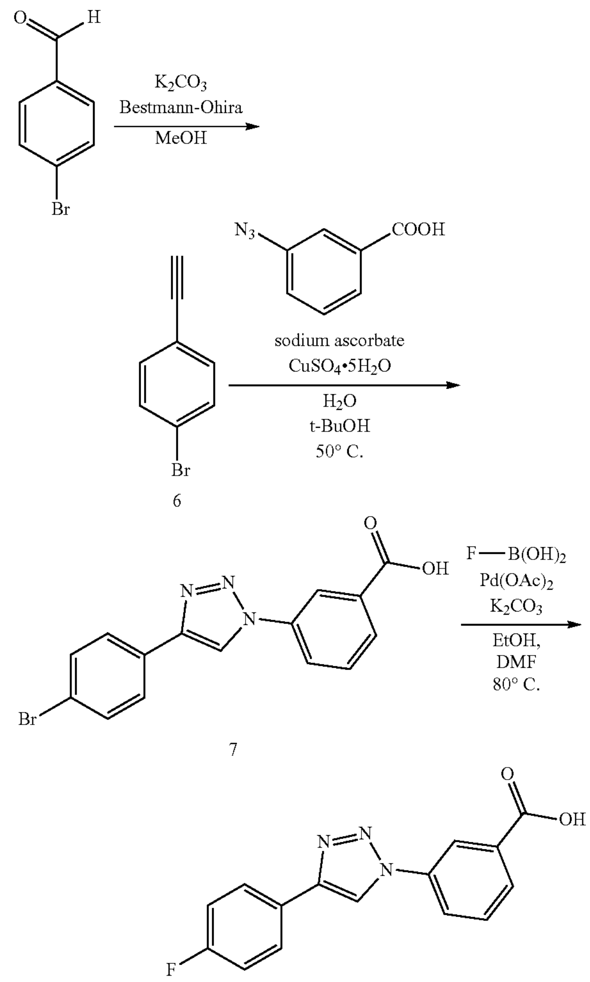

Compounds of Formula VII are synthesized using Suzuki cross-coupling reaction. While boronic acids are commercially available or can be synthesized following synthetic methodologies known in the art, the aryl bromide 7 is prepared starting from 4-bromobenzaldehyde that reacts in the presence of Bestmann-Ohira reagent, affording intermediate 6. 6 reacts with 3-azidobenzoic acid via the azide-alkyne 1,3-dipolar cycloaddition catalyzed by copper (I) generated in situ by sodium ascorbate affording compound 7.

Compounds of formula (VIII)

(VIII)

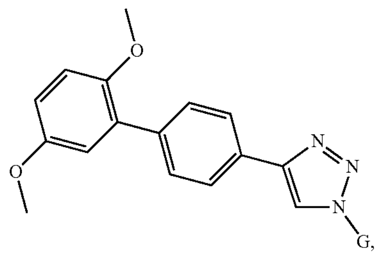

wherein G is selected from pyridin-4-yl, pyridin-3-yl), pyridin-2-yl, 3-fluoropyridin-4-yl, 3-carboxyphenyl, 2-carboxypyridin-4-yl and (2-methoxycarbonyl)pyridin-4-yl, can be prepared as outlined in Scheme e below:

Scheme e

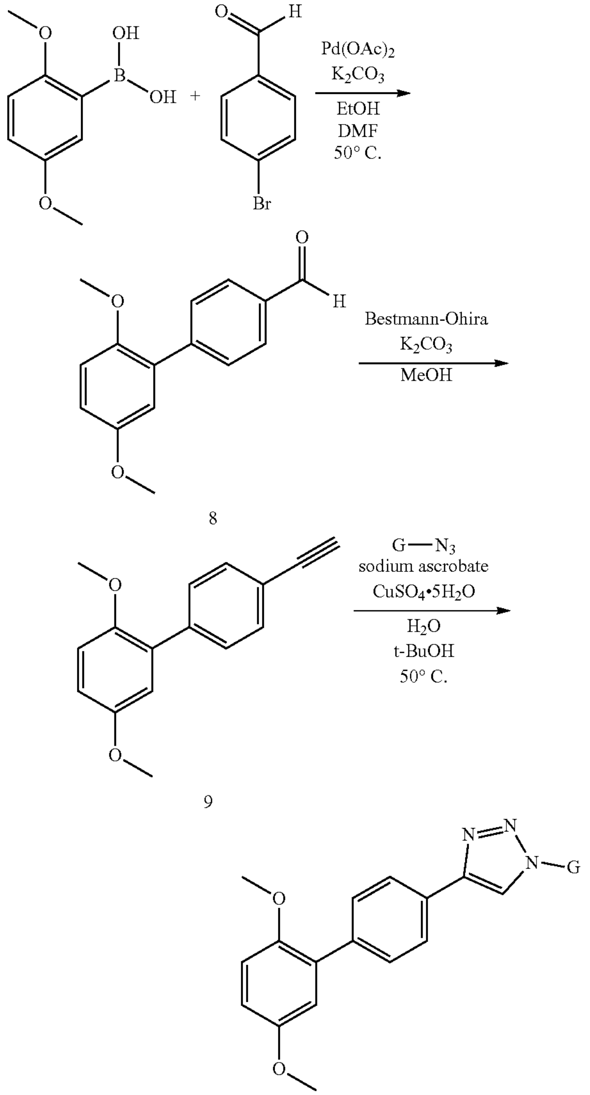

Compounds of Formula VIII are synthesized via the azide-alkyne 1,3-dipolar cycloaddition catalyzed by copper (I) generated in situ by sodium ascorbate. While azides are synthesized following synthetic methodologies known in the art, the alkyne 9 is prepared as depicted in Scheme e. The (2,5-dimethoxyphenyl)boronic acid and the 4-bromobenzaldehyde react in a Suzuki cross-coupling reaction to give intermediate 8. Then, 8 reacts in the presence of Bestmann-Ohira reagent, affording the alkyne 9 (intermediate 9).

The chemical reactions described in the Examples below may be readily adapted to prepare a number of other SOCE modulators of the present invention, and alternative methods for preparing the compounds of formula (I) belong to the common general knowledge of the skilled man.

For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1: Synthesis of 3-(1-(4-bromophenyl)-1H-1,2,3-triazol-4-yl)benzoic acid (Intermediate 1)

To a suspension of 1-azido-4-bromobenzene (2.78 g, 14.04 mmol) in water (26 mL) and t-BuOH (26 mL) 3-ethynylbenzoic acid (2.05 g, 14.04 mmol) is added. Then, 1.4 mL of an aqueous solution of sodium ascorbate 1M and copper sulfate pentahydrate (34.9 mg, 0.14 mmol) are added and the mixture is vigorously stirred for 48 h. The volatile is then removed and the crude product is purified by column chromatography using petroleum ether/ethyl acetate 2:8 and ethyl acetate/methanol 8:2 as eluents, yielding compound 1 as a yellow solid (4.22 g, 12.27 mmol, 87%).

Analytical Data $^1$H-NMR (300 MHz, DMSO-$d_6$): δ 9.54 (s, 1H), 8.51 (s, 1H), 8.14 (d, J=7.7 Hz, 1H), 7.98-7.94 (m, 3H), 7.86-7.83 (d, J=8.8 Hz, 2H), 7.60 (t, J=7.7 Hz, 1H). MS: M−1 343.

Example 2: Synthesis of 2',5'-dimethoxy-[1,1'-biphenyl]-4-amine (Intermediate 2)

4-Bromoaniline (2 g, 11.63 mmol) is solubilized in DMF (23 mL) and ethanol (23 mL) under nitrogen atmosphere. 2,5-Dimethoxyphenyl)boronic acid (3.17 g, 17.44 mmol), $Pd(OAc)_2$ (26.1 mg, 0.116 mmol) and $K_2CO_3$ (3.2 g, 23.26 mmol) are added in order. The mixture is stirred at 80° C. for 3 h and at room temperature overnight. The reaction is filtered under vacuo over a pad of celite, rinsed with ethanol and evaporated. The crude product is purified by column chromatography using petroleum ether/ethyl acetate 7:3 as eluent, yielding compound 2 as a yellow solid (2.61 g, 11.40 mmol, 98%).

Analytical Data $^1$H-NMR (300 MHz, $CDCl_3$): δ 7.39 (d, J=6.9 Hz, 2H), 6.97-6.88 (m, 2H), 6.84 (s, 1H), 6.70 (d, J=6.9 Hz, 2H), 3.82 (s, 3H), 3.76 (s, 3H). MS: M+1 230.

Example 3: Synthesis of 4'-azido-2,5-dimethoxy-1,1'-biphenyl (Intermediate 3)

To a solution of 2',5'-dimethoxy-[1,1'-biphenyl]-4-amine (2 g, 8.73 mmol) in water (40 mL) HCl 37% (3.5 mL) is added and the resulting mixture is cooled down at 0° C. Then, a solution of $NaNO_2$ (0.60 g, 8.73 mmol) in water (2 mL) is added and, after 10 min, a solution of $NaN_3$ (0.68 g, 10.48 mmol) in water (2 mL) is added dropwise. The reaction is stirred at room temperature for 5 h, diluted with EtOAc and washed with water (2×). The organic layer is dried over sodium sulfate and the volatile is removed under vacuo. The crude material is purified by column chromatography using petroleum ether/ethyl acetate 98:2 as eluent, yielding compound 3 as an orange solid (1.33 g, 5.24 mmol, 60%).

Analytical Data $^1$H-NMR (300 MHz, $CDCl_3$): δ 8.31 (d, J=7.1 Hz, 2H), 7.75 (d, J=7.1 Hz, 2H), 6.92-6.83 (m, 3H), 3.85 (s, 3H), 3.79 (s, 3H).

Example 4: Synthesis of 4-(2,3-dihydrobenzo[b][1,4]dioxin-6-yl)aniline (Intermediate 4)

4-Bromoaniline (0.5 g, 2.91 mmol) is solubilized in DMF (5 mL) and ethanol (5 mL) under nitrogen atmosphere. (2,3-Dihydrobenzo[b][1,4]dioxin-6-yl)boronic acid (0.52 g, 2.91 mmol), $Pd(OAc)_2$ (19.6 mg, 0.029 mmol) and $K_2CO_3$ (0.80 g, 5.82 mmol) are added in order. The mixture is stirred at 80° C. for 6 h and at room temperature overnight. The reaction is filtered under vacuo over a pad of celite, rinsed with ethanol and evaporated. The crude product is purified by column chromatography using petroleum ether/ethyl acetate 8:2 as eluent, yielding compound 4 as an orange solid (0.65 g, 2.86 mmol, 98%).

Analytical Data $^1$H-NMR (300 MHz, $CDCl_3$): δ 7.37 (d, J=7.9 Hz, 2H), 7.09 (s, 1H), 7.04 (d, J=8.2 Hz, 1H), 6.93 (d, J=8.2 Hz, 1H), 6.72 (d, J=7.9 Hz, 2H), 4.26-4.23 (m, 4H). MS: M+1 228.

Example 5: Synthesis of 6-(4-azidophenyl)-2,3-dihydrobenzo[b][1,4]dioxine (Intermediate 5)

To a solution of 2',5'-dimethoxy-[1,1'-biphenyl]-4-amine (475 mg, 2.09 mmol) in water (9 mL) HCl 37% (831 μL) is added and the resulting mixture is cooled down at 0° C. Then, a solution of $NaNO_2$ (144 mg, 2.09 mmol) in water (2 mL) is added and, after 10 min, a solution of $NaN_3$ (163 mg, 2.51 mmol) in water (2 mL) is added dropwise. The reaction is stirred at room temperature for 1 h, diluted with EtOAc and washed with water (1×) and with aqueous solution of HCl 3N (1×). The organic layer is dried over sodium sulfate and the volatile is removed under vacuo. The crude material is purified by column chromatography using petroleum ether/ethyl acetate 98:2 as eluent, yielding compound 5 as a dark yellow solid (386 mg, 1.53 mmol, 73%).

Analytical Data $^1$H-NMR (300 MHz, $CDCl_3$): δ 7.50 (d, J=6.8 Hz, 2H), 7.10-7.07 (m, 4H), 6.92 (d, J=7.7 Hz, 1H), 4.28-4.22 (m, 4H).

Example 6: Synthesis of 1-bromo-4-ethynylbenzene (Intermediate 6)

To a solution of 4-bromobenzaldehyde (2.15 g, 11.62 mmol) in MeOH (22 mL) $K_2CO_3$ (3.21 g, 23.24 mmol) and dimethyl (1-diazo-2-oxopropyl)phosphonate (2.61 g, 17.43 mmol) are added in order under nitrogen. The mixture is stirred at room temperature overnight, then the solvent is removed under vacuo, water is added and the aqueous layer is extracted with $CH_2Cl_2$(5×). The organic phases are collected, dried over sodium sulfate and evaporated. The crude material is purified by column chromatography using petroleum ether/ethyl acetate 9:1 and petroleum ether/ethyl acetate 8:2 as eluents, yielding compound 6 as an orange solid (1.12 g, 6.26 mmol, 54%).

Analytical Data $^1$H-NMR (300 MHz, $CDCl_3$): δ 7.45 (d, J=8.5 Hz, 2H), 7.34 (d, J=8.5 Hz, 2H), 3.11 (s, 1H). MS: M+1 180.

Example 7: Synthesis of 3-(4-(4-bromophenyl)-1H-1,2,3-triazol-1-yl)benzoic acid (Intermediate 7)

To a suspension of 1-bromo-4-ethynylbenzene (1 g, 5.52 mmol) in water (6 mL) and t-BuOH (6 mL) 3-azidobenzoic acid (0.89 g, 5.52 mmol) is added. Then, 55 μL of an aqueous solution of sodium ascorbate 1M and copper sulfate pentahydrate (13.7 mg, 0.055 mmol) are added and the mixture is vigorously stirred overnight. The volatile is then removed and the crude material is purified by column chromatography using petroleum ether/ethyl acetate 3:7 and ethyl acetate as eluents, yielding compound 7 as a pale yellow solid (1.23 g, 3.59 mmol, 65%).

Analytical Data $^1$H-NMR (300 MHz, DMSO-$d_6$): δ 9.50 (s, 1H), 8.46 (s, 1H), 8.19 (d, J=7.6 Hz, 1H), 8.06 (d, J=7.6 Hz, 1H), 7.92 (d, J=8.5 Hz, 2H), 7.78-7.69 (m, 3H). MS: M−1 343.

Example 8: Synthesis of 2',5'-dimethoxy-[1,1'-biphenyl]-4-carbaldehyde (Intermediate 8)

To a solution of 4-bromobenzaldehyde (500 mg, 2.70 mmol) in DMF (8 mL) and water (2 mL) (2,5-dimethoxyphenyl)boronic acid (540 mg, 2.97 mmol), $Pd(OAc)_2$ (11.2 mg, 0.05 mmol) and $K_2CO_3$ (933 mg, 6.75 mmol) are added in order under nitrogen atmosphere. The mixture is stirred at 50° C. for 3 h. The reaction is filtered under vacuo over a pad of celite, diluted with diethyl ether and washed with water (3×). The organic phase is dried over sodium sulphate and evaporated. The crude product is purified by column chromatography using petroleum ether/ethyl acetate 98:2 as eluent, yielding compound 8 as an orange solid (647 mg, 2.67 mmol, 99%).

Analytical Data $^1$H-NMR (300 MHz, $CDCl_3$): δ 10.06 (s, 1H), 7.89 (d, J=7.7 Hz, 2H), 7.69 (d, J=7.7 Hz, 2H), 7.08-6.91 (m, 3H), 3.79 (s, 3H), 3.73 (s, 3H). MS: M+1 243.

Example 9: Synthesis of 4'-ethynyl-2,5-dimethoxy-1,1'-biphenyl (Intermediate 9)

To a solution of 2',5'-dimethoxy-[1,1'-biphenyl]-4-carbaldehyde (636 mg, 2.63 mmol) in MeOH (6 mL) $K_2CO_3$ (727 mg, 5.26 mmol) and dimethyl (1-diazo-2-oxopropyl)phosphonate (759 mg, 3.95 mmol) are added in order under nitrogen. The mixture is stirred at room temperature overnight, then the solvent is removed, water is added and the aqueous layer is extracted with $CH_2Cl_2$ (3×). The organic phases are collected, dried over sodium sulfate and evaporated. The crude material is purified by column chromatography using petroleum ether/ethyl acetate 98:2 as eluent, yielding compound 9 as a white solid (514 mg, 2.16 mmol, 82%).

Analytical Data $^1$H-NMR (300 MHz, $CDCl_3$): δ 7.59-7.49 (m, 4H), 6.93-6.85 (m, 3H), 3.86 (s, 3H), 3.76 (s, 3H), 3.10 (s, 1H). MS: M+1 239.

Example 10: Synthesis of 3-(1-([1,1'-biphenyl]-4-yl)-1H-1,2,3-triazol-4-yl)benzoic acid (10)

3-(1-(4-Bromophenyl)-1H-1,2,3-triazol-4-yl)benzoic acid (100 mg, 0.29 mmol) is solubilized in DMF (500 μL) and ethanol (500 μL) under nitrogen atmosphere. Phenylboronic acid (79 mg, 0.44 mmol), $Pd(OAc)_2$ (1.96 mg, 0.0029 mmol) and $K_2CO_3$ (80 mg, 0.58 mmol) are added in order. The mixture is stirred at 80° C. for 3 h and at room temperature overnight. The reaction is filtered under vacuo over a pad of celite, rinsed with ethanol and evaporated. The crude product is purified by column chromatography using petroleum ether/ethyl acetate 4:6 as eluent, yielding compound 10 as a yellow solid (39.5 mg, 0.12 mmol, 40%).

Analytical Data $^1$H-NMR (300 MHz, DMSO-$d_6$): δ 9.52 (s, 1H), 8.61 (s, 1H), 8.20 (d, J=6.9 Hz, 1H), 8.09 (d, J=8.3 Hz, 2H), 7.98-7.85 (m, 3H), 7.77 (d, J=8.3 Hz, 2H), 7.63 (t, J=7.5 Hz, 1H), 7.54-7.50 (m, 2H), 7.43 (d, J=7.5 Hz, 1H). MS: M+1 342.

Example 11: Synthesis of 3-(1-(3'-(methylthio)-[1,1'-biphenyl]-4-yl)-1H-1,2,3-triazol-4-yl)benzoic acid (11)

The title compound is synthesized following the procedure described for Example 10. The crude product is purified by column chromatography using ethyl acetate/methanol 9:1 as eluent, yielding compound 11 as a white solid (89.8 mg, 0.23 mmol, 80%).

Analytical Data $^1$H-NMR (300 MHz, DMSO-$d_6$): δ 9.55 (s, 1H), 8.55 (s, 1H), 8.18 (d, J=7.9 Hz, 1H), 8.08 (d, J=9.3 Hz, 2H), 7.97-7.95 (m, 3H), 7.60 (d, J=9.3 Hz, 2H), 7.52 (d, J=7.9 Hz, 1H), 7.45 (t, J=7.9 Hz, 1H), 7.31 (d, J=6.2 Hz, 1H), 2.58 (s, 3H). MS: M+1 388.

Example 12: Synthesis of 3-(1-(2'-methoxy-[1,1'-biphenyl]-4-yl)-1H-1,2,3-triazol-4-yl)benzoic acid (12)

The title compound is synthesized following the procedure described for Example 10. The crude product is purified by column chromatography using ethyl acetate as eluent, yielding compound 12 as a yellow solid (72 mg, 0.19 mmol, 67%).

Analytical Data $^1$H-NMR (300 MHz, DMSO-$d_6$): δ 9.45 (s, 1H), 8.56 (s, 1H), 8.18 (d, J=6.9 Hz, 1H), 8.03-7.95 (m, 3H), 7.74 (d, J=8.3 Hz, 2H), 7.53 (t, J=6.9 Hz, 1H), (d, J=8.3 Hz, 2H), 7.24-7.14 (m, 2H), 3.82 (s, 3H). MS: M+1 372.

Example 13: Synthesis of 3-(1-(3'-Methoxy-[1,1'-biphenyl]-4-yl)-1H-1,2,3-triazol-4-yl)benzoic acid (13)

The title compound is synthesized following the procedure described for Example 10. The crude product is purified by column chromatography using ethyl acetate/methanol 9:1 as eluent, yielding compound 13 as a white solid (73 mg, 0.20 mmol, 68%).

Analytical Data $^1$H-NMR (300 MHz, DMSO-$d_6$): 9.45 (s, 1H), 8.54 (s, 1H), 8.19 (d, J=7.4 Hz, 1H), 8.05 (d, J=7.8 Hz, 2H), 7.94-7.91 (m, 3H), 7.64 (t, J=7.4 Hz, 1H), 7.42 (d, J=6.8 Hz, 1H), 7.32 (d, J=6.8 Hz, 1H), 7.28 (s, 1H), 6.98 (d, J=7.4 Hz, 1H), 3.84 (s, 3H). MS: M+1 372.

Example 14: Synthesis of 3-(1-(3'-hydroxy-[1,1'-biphenyl]-4-yl)-1H-1,2,3-triazol-4-yl)benzoic acid (14)

The title compound is synthesized following the procedure described for Example 10. The crude product is purified by column chromatography using ethyl acetate/methanol 9:1 and ethyl acetate/methanol 8:2 as eluents, yielding compound 14 as a dark yellow solid (19 mg, 0.05 mmol, 18%).

Analytical Data $^1$H-NMR (300 MHz, $CD_3OD$): δ 8.96 (s, 1H), 8.59 (s, 1H), 8.15 (s, 1H), 8.03 (d, J=7.8 Hz, 1H), 7.92 (d, J=7.4 Hz, 1H), 7.58 (d, J=7.8 Hz, 1H), 7.18-7.15 (m, 3H), 7.04-6.99 (m, 2H), 6.82 (d, J=5.8 Hz, 2H). MS: M−1 356.

Example 15: Synthesis of 3-(1-(2',4'-dimethoxy-[1, 1'-biphenyl]-4-yl)-1H-1,2,3-triazol-4-yl)benzoic acid (15)

The title compound is synthesized following the procedure described for Example 10. The crude product is purified by column chromatography using ethyl acetate/methanol 9:1 as eluent, yielding compound 15 as a pale yellow solid (100 mg, 0.25 mmol, 86%).

Analytical Data $^1$H-NMR (300 MHz, DMSO-$d_6$): δ 9.47 (s, 1H), 8.56 (s, 1H), 8.17 (d, J=8.2 Hz, 1H), 7.99-7.95 (m, 3H), 7.69 (d, J=9.2 Hz, 2H), 7.62 (t, J=8.2 Hz, 1H) 7.32 (d, J=8.2 Hz, 1H), 6.71 (s, 1H), 6.66 (d, J=6.2 Hz, 1H), 3.83 (s, 3H), 3.81 (s, 3H). MS: M+1 402.

Example 16: Synthesis of 3-(1-(3',5'-dimethoxy-[1, 1'-biphenyl]-4-yl)-1H-1,2,3-triazol-4-yl)benzoic acid (16)

The title compound is synthesized following the procedure described for Example 10. The crude product is purified by column chromatography using ethyl acetate/methanol 9:1 as eluent, yielding compound 16 as a white solid (100 mg, 0.25 mmol, 86%).

Analytical Data $^1$H-NMR (300 MHz, DMSO-$d_6$): δ 9.51 (s, 1H), 8.56 (s, 1H), 8.17 (d, J=7.4 Hz, 1H), 8.06 (d, J=8.2 Hz, 2H), 7.95-7.93 (m, 3H), 7.61 (t, J=7.4 Hz, 1H), 6.89 (s, 2H), 6.55 (s, 1H), 3.83 (s, 3H), 3.73 (s, 3H). MS: M+1 402.

Example 17: Synthesis of 3-(1-(4-(benzo[d][1,3]dioxol-5-yl)phenyl)-1H-1,2,3-triazol-4-yl)benzoic acid (17)

The title compound is synthesized following the procedure described for Example 10. The crude product is purified by column chromatography using ethyl acetate/methanol 9:1 as eluent, yielding compound 17 as a yellow solid (37 mg, 0.10 mmol, 33%).

Analytical Data $^1$H-NMR (300 MHz, DMSO-$d_6$): δ 9.51 (s, 1H), 8.54 (s, 1H), 8.17 (d, J=7.4 Hz, 1H), 8.03 (d, J=8.5 Hz, 2H), 7.95 (d, J=7.9 Hz, 1H), 7.87 (d, J=8.5 Hz, 2H), 7.61 (t, J=7.4 Hz, 1H), 7.42 (s, 1H), 7.27 (d, J=7.9 Hz, 1H), 7.04 (d, J=7.4 Hz, 1H), 6.09 (s, 2H). MS: M+1 386.

Example 18: Synthesis of 3-(1-(4-(2,3-dihydrobenzo[b][1,4]dioxin-6-yl)phenyl)-1H-1,2,3-triazol-4-yl)benzoic acid (18)

The title compound is synthesized following the procedure described for Example 10. The crude product is purified by column chromatography using ethyl acetate/methanol 9:1 as eluent, yielding compound 18 as a white solid (87 mg, 0.22 mmol, 75%).

Analytical Data $^1$H-NMR (300 MHz, DMSO-$d_6$): δ 9.50 (s, 1H), 8.55 (s, 1H), 8.03-7.94 (m, 4H), 7.86 (d, J=7.9 Hz, 2H), 7.62 (t, J=8.2 Hz, 1H), 7.27-7.23 (m, 2H), 6.97 (d, J=8.2 Hz, 1H), 4.29-4.22 (m, 4H). MS: M+1 400.

Example 19: Synthesis of 3-(1-(3',4'-dimethoxy-[1, 1'-biphenyl]-4-yl)-1H-1,2,3-triazol-4-yl)benzoic acid (19)

The title compound is synthesized following the procedure described for Example 10. The crude product is purified by column chromatography using ethyl acetate/methanol 9:1 and ethyl acetate/methanol 8:2 as eluents, yielding compound 19 as a pale yellow solid (50 mg, 0.12 mmol, 43%).

Analytical Data $^1$H-NMR (300 MHz, DMSO-$d_6$): δ 9.47 (s, 1H), 8.55 (s, 1H), 8.17 (d, J=7.1 Hz, 1H), 8.03 (d, J=8.2 Hz, 2H), 7.97-7.90 (m, 3H), 7.62 (t, J=7.9 Hz, 1H), 7.33-7.29 (m, 2H), 7.07 (d, J=7.9 Hz, 1H), 3.99 (s, 3H), 3.88 (s, 3H). MS: M+1 402.

Example 20: Synthesis of 3-(1-(2',3'-dimethoxy-[1, 1'-biphenyl]-4-yl)-1H-1,2,3-triazol-4-yl)benzoic acid (20)

The title compound is synthesized following the procedure described for Example 10. The crude product is purified by column chromatography using ethyl acetate/methanol 9:1 and ethyl acetate/methanol 8:2 as eluents, yielding compound 20 as a yellow solid (88 mg, 0.22 mmol, 76%).

Analytical Data $^1$H-NMR (300 MHz, DMSO-$d_6$): δ 9.46 (s, 1H), 8.57 (s, 1H), 8.18 (d, J=6.8 Hz, 1H), 8.05 (d, J=7.1 Hz, 2H), 7.98 (d, J=6.8 Hz, 1H), 7.74 (d, J=7.1 Hz, 2H), 7.64 (t, J=6.8 Hz, 1H), 7.18-7.14 (m, 2H), 7.03 (t, J=7.3 Hz, 1H) 3.88 (s, 3H), 3.77 (s, 3H). MS: M+1 402.

Example 21: Synthesis of 3-(1-(4-(2,3-dihydrobenzo[b][1,4]dioxin-5-yl)phenyl)-1H-1,2,3-triazol-4-yl)benzoic acid (21)

The title compound is synthesized following the procedure described for Example 10. The crude product is purified by column chromatography using ethyl petroleum ether/acetate 1:9 and ethyl acetate/methanol 9:1 as eluents, yielding compound 21 as a pale yellow solid (88 mg, 0.22 mmol, 76%).

Analytical Data $^1$H-NMR (300 MHz, DMSO-$d_6$): δ 9.44 (s, 1H), 8.55 (s, 1H), 8.15 (d, J=5.9 Hz, 1H), 8.03-7.97 (m, 3H), 7.67 (d, J=8.5 Hz, 2H), 7.61 (t, J=7.5 Hz, 1H), 6.94-6.93 (m, 3H), 4.32-4.28 (m, 4H). MS: M+1 400.

Example 22: Synthesis of 3-(1-(2',6'-dimethoxy-[1, 1'-biphenyl]-4-yl)-1H-1,2,3-triazol-4-yl)benzoic acid (22)

The title compound is synthesized following the procedure described for Example 10. The crude product is purified by column chromatography using ethyl acetate/methanol 9:1 and ethyl acetate/methanol 8:2 as eluents, yielding compound 22 as a pale yellow solid (60 mg, 0.15 mmol, 52%).

Analytical Data $^1$H-NMR (300 MHz, DMSO-$d_6$): δ 9.40 (s, 1H), 8.55 (s, 1H), 8.15 (d, J=6.9 Hz, 1H), 7.97-7.95 (m, 4H), 7.84 (d, J=6.9 Hz, 1H), 7.62-7.58 (m, 1H), 7.47 (d, J=8.2 Hz, 1H), 7.35 (t, J=8.2 Hz, 1H), 6.79 (d, J=8.2 Hz, 1H), 3.71 (s, 6H). MS: M+1 402.

Example 23: Synthesis of 3-(1-(2'-fluoro-5'-methoxy-[1,1'-biphenyl]-4-yl)-1H-1,2,3-triazol-4-yl) benzoic acid (23)

The title compound is synthesized following the procedure described for Example 10. The crude product is purified by column chromatography using ethyl acetate/methanol 9:1 as eluent, yielding compound 23 as a white solid (52 mg, 0.13 mmol, 46%).

Analytical Data $^1$H-NMR (300 MHz, DMSO-$d_6$): δ 9.45 (s, 1H), 8.54 (s, 1H), 8.16 (d, J=7.1 Hz, 1H), 8.08 (d, J=7.8 Hz, 2H), 7.95 (d, J=7.1 Hz, 1H), 7.82 (d, J=7.8 Hz, 2H), 7.64-7.59 (m, 1H), 7.27 (t, J=7.1 Hz, 1H), 7.13-7.12 (m, 1H), 7.01-6.98 (m, 1H), 3.81 (s, 3H). MS: M+1 390.

Example 24: Synthesis of 3-(1-(2',5'-dimethoxy-[1,1'-biphenyl]-4-yl)-1H-1,2,3-triazol-4-yl)benzoic acid (24)

To a suspension of 4'-azido-2,5-dimethoxy-1,1'-biphenyl (74 mg, 0.29 mmol) in water (460 μL) and t-BuOH (460 μL) 3-ethynylbenzoic acid (42 mg, 0.29 mmol) is added. Then, 29 μL of an aqueous solution of sodium ascorbate 1M and copper sulfate pentahydrate (0.72 mg, 0.0029 mmol) are added and the mixture is vigorously stirred overnight. The volatile is then removed and the crude product is purified by column chromatography using petroleum ether/ethyl acetate 6:4 as eluent, yielding compound 24 as a pale yellow solid (49 mg, 0.12 mmol, 42%).

Analytical Data $^1$H-NMR (300 MHz, $CDCl_3$): δ 9.20 (s, 1H), 8.66 (s, 1H), 8.28 (d, J=8.0 Hz, 1H), 8.04 (d, J=6.6 Hz, 2H), 7.73 (d, J=6.6 Hz, 2H), 7.67-7.53 (m, 2H), 7.08 (d, J=8.0 Hz, 1H), 7.01-6.92 (m, 2H), 3.82 (s, 3H), 3.79 (s, 3H). MS: M+1 402.

Example 25: Synthesis of 4-(1-(2',5'-dimethoxy-[1,1'-biphenyl]-4-yl)-1H-1,2,3-triazol-4-yl)picolinic acid (25)

Methyl 4-(1-(2',5'-dimethoxy-[1,1'-biphenyl]-4-yl)-1H-1,2,3-triazol-4-yl)picolinate is synthesized following the procedure described for Example 24. The crude product is purified by column chromatography using petroleum ether/ethyl acetate 4:6 as eluent, yielding methyl 4-(1-(2',5'-dimethoxy-[1,1'-biphenyl]-4-yl)-1H-1,2,3-triazol-4-yl)picolinate as a yellow solid (39 mg, 0.09 mmol, 32%).

The compound (39 mg, 0.09 mmol) is solubilized in acetone (390 μL) and water (390 μL). NaOH (7.2 mg, 0.18 mmol) is added and the mixture is stirred at room temperature for 1 h. The volatile is then removed and the crude product is purified by column chromatography using ethyl acetate/methanol 7:3 as eluent, yielding compound 25 as a pale yellow solid (21 mg, 0.05 mmol, 58%).

Analytical Data $^1$H-NMR (300 MHz, DMSO-$d_6$): δ 9.72 (s, 1H), 8.70-8.56 (m, 3H), 8.01 (d, J=8.0 Hz, 2H), 7.75 (d, J=8.0 Hz, 2H), 7.75 (s, 1H), 6.96 (m, 2H), 3.76 (s, 3H), 3.73 (s, 3H). MS: M+1 403.

Example 26: Synthesis of 4-(1-(2',5'-dimethoxy-[1,1'-biphenyl]-4-yl)-1H-1,2,3-triazol-4-yl)-3-fluoropyridine (26)

The title compound is synthesized following the procedure described for Example 24. The crude product is purified by column chromatography using with petroleum ether/ethyl acetate 6:4 as eluent, yielding compound 26 as a yellow solid (34 mg, 0.09 mmol, 31%).

Analytical Data $^1$H-NMR (300 MHz, $CDCl_3$): δ 8.60-8.50 (m, 3H), 8.31 (d, J=6.1 Hz, 1H), 7.85 (d, J=8.5 Hz, 2H), 7.73 (d, J=8.5 Hz, 2H), 6.97-6.89 (m, 3H), 3.83 (s, 3H), 3.75 (s, 3H). MS: M+1 377.

Example 27: Synthesis of 4-(1-(2',5'-dimethoxy-[1,1'-biphenyl]-4-yl)-1H-1,2,3-triazol-4-yl)pyridine (27)

The title compound is synthesized following the procedure described for Example 24. The crude product is purified by column chromatography using petroleum ether/ethyl acetate 4:6 as eluent, yielding compound 27 as a whitish solid (38 mg, 0.11 mmol, 37%).

Analytical Data $^1$H-NMR (300 MHz, $CDCl_3$): δ 8.36 (s, 1H), 7.82 (d, J=7.4 Hz, 2H), 7.73-7.64 (m, 4H), 7.52 (s, 1H), 6.97-6.90 (m, 4H), 3.82 (s, 3H), 3.80 (s, 3H). MS: M+1 359.

Example 28: Synthesis of 3-(1-(2',5'-dimethoxy-[1,1'-biphenyl]-4-yl)-1H-1,2,3-triazol-4-yl)pyridine (28)

The title compound is synthesized following the procedure described for Example 24. The crude product is purified by column chromatography using petroleum ether/ethyl acetate 5:5, petroleum ether/ethyl acetate 3:7 and petroleum ether/ethyl acetate 2:8 as eluents, yielding compound 28 as a yellow solid (68 mg, 0.19 mmol, 65%).

Analytical Data $^1$H-NMR (300 MHz, $CDCl_3$): δ 9.11 (s, 1H), 8.63 (s, 1H), 8.31-8.29 (m, 2H), 7.83 (d, J=8.3 Hz, 2H), 7.72 (d, J=8.3 Hz, 2H), 7.43 (s, 1H), 6.97-6.91 (m, 3H), 3.94 (s, 3H), 3.79 (s, 3H). MS: M+1 359.

Example 29: Synthesis of 2-(1-(2',5'-dimethoxy-[1,1'-biphenyl]-4-yl)-1H-1,2,3-triazol-4-yl)pyridine (29)

The title compound is synthesized following the procedure described for Example 24. The crude product is purified by column chromatography using petroleum ether/ethyl acetate 7:3 as eluent, yielding compound 29 as a yellow solid (52 mg, 0.15 mmol, 50%).

Analytical Data $^1$H-NMR (300 MHz, $CDCl_3$): δ 8.65-8.59 (m, 2H), 8.26 (d, J=8.0 Hz, 1H), 7.85-7.78 (m, 3H), 7.70 (d, J=8.5 Hz, 2H), 7.25 (t, J=6.6 Hz, 1H), 6.95-6.86 (m, 3H), 3.82 (s, 3H), 3.77 (s, 3H). MS: M+1 359.

Example 30: Synthesis of 3-(1-(4-(2,3-dihydrobenzo[b][1,4]dioxin-6-yl)phenyl)-1H-1,2,3-triazol-4-yl)benzonitrile (30)

To a solution of $Cu(OAc)_2$ (5.27 mg, 0.029 mmol) in THF (53 μL) TBTA (tris(benzyltriazolylmethyl)amine) (15 mg, 0.029 mmol) is added and the mixture is stirred at room temperature for 30 min. A solution of intermediate 3 (150 mg, 0.58 mmol) in THF (1 mL), a solution of 3-ethynylbenzonitrile (74 mg, 0.58 mmol) in THF (1 mL) and 58 μL of an aqueous solution of sodium ascorbate 1M are added in order. The reaction is stirred at room temperature for 3 h. The volatile is removed and the crude product is purified by column chromatography using ethyl acetate/methanol 9:1 as eluent, yielding compound 30 as a yellow solid (198 mg, 0.52 mmol, 90%).

Analytical Data $^1$H-NMR (300 MHz, DMSO-$d_6$): δ 9.45 (s, 1H), 8.35 (s, 1H), 8.30 (d, J=7.7 Hz, 1H), 7.94 (d, J=7.9 Hz, 2H), 7.88-7.86 (m, 3H), 7.73 (t, J=7.4 Hz, 1H), 7.26-7.23 (m, 2H), 6.97 (d, J=7.4 Hz, 1H), 4.31-4.28 (m, 4H). MS: M+1 381.

Example 31: Synthesis of 5-(3-(1-(4-(2,3-dihydrobenzo[b][1,4]dioxin-6-yl)phenyl)-1H-1,2,3-triazol-4-yl)phenyl)-1H-tetrazole (31)

Compound 30 (100 mg, 0.26 mmol) is solubilized in DMF (3 mL), $NaN_3$ (20 mg, 0.31 mmol) and $NH_4Cl$ (16 mg, 0.31 mmol) are added in order. The mixture is stirred at 120° C. for 48 h. Then, HCl 3N is added dropwise until pH 6. The aqueous layer is extracted with ethyl acetate (6×) and the organic phases are collected, dried over sodium sulfate and evaporated. The crude product is purified by column chromatography using petroleum ether/ethyl acetate 2:8 and ethyl acetate as eluents, yielding compound 31 as a dark yellow solid (39 mg, 0.09 mmol, 35%).

Analytical Data $^1$H-NMR (300 MHz, $CD_3OD$): δ 8.94 (s, 1H), 8.42 (s, 1H), 7.95 (d, J=8.2 Hz, 2H), 7.76 (d, J=8.2 Hz, 2H), 7.66 (t, J=7.1 Hz, 1H), 7.37-7.33 (m, 2H), 7.17-7.15 (m, 2H), 6.98 (d, J=7.1 Hz, 1H), 4.30-4.27 (m, 4H). MS: M+1 424.

Example 32: Synthesis of 2-(3-(1-(4-(2,3-dihydrobenzo[b][1,4]dioxin-6-yl)phenyl)-1H-1,2,3-triazol-4-yl)phenyl)acetic acid (32)

The title compound is synthesized following the procedure described for Example 30. The crude product is purified by column chromatography using ethyl acetate and ethyl acetate/methanol 8:2 as eluents, yielding compound 32 as a dark yellow solid (98 mg, 0.24 mmol, 41%).

Analytical Data $^1$H-NMR (300 MHz, DMSO-$d_6$): δ 9.21 (s, 1H), 8.02 (s, 1H), 7.87-7.80 (m, 4H), 7.40 (d, J=7.9 Hz, 2H), 7.26 (t, J=8.5 Hz, 1H), 7.25-7.20 (m, 3H), 5.51 (s, 2H), 4.30-4.27 (m, 4H). MS: M+1 414.

Example 33: Synthesis of 3-(4-([1,1'-biphenyl]-4-yl)-1H-1,2,3-triazol-1-yl)benzoic acid (33)

3-(4-(4-Bromophenyl)-1H-1,2,3-triazol-1-yl)benzoic acid (100 mg, 0.29 mmol) is solubilized in DMF (500 μL) and ethanol (500 μL) under nitrogen atmosphere. Phenylboronic acid (79 mg, 0.44 mmol), $Pd(OAc)_2$ (1.96 mg, 0.0029 mmol) and $K_2CO_3$ (80 mg, 0.58 mmol) are added in order. The mixture is stirred at 80° C. for 3 h and at room temperature overnight. The reaction is filtered under vacuo over a pad of celite, rinsed with ethanol and evaporated. The crude product is purified by column chromatography using ethyl acetate as eluent, yielding compound 33 as a white solid (54 mg, 0.16 mmol, 55%).

Analytical Data $^1$H-NMR (300 MHz, DMSO-$d_6$): δ 9.48 (s, 1H), 8.48 (s, 1H), 8.13-8.03 (m, 5H), 7.83-7.69 (m, 4H), 7.49 (m, 2H), 7.38 (d, J=7.1 Hz, 1H). MS: M+1 342.

Example 34: Synthesis of 3-(4-(3'-(methylthio)-[1,1'-biphenyl]-4-yl)-1H-1,2,3-triazol-1-yl)benzoic acid (34)

The title compound is synthesized following the procedure described for Example 33. The crude product is purified by column chromatography using petroleum ether/ethyl acetate 5:5 as eluent, yielding compound 34 as a yellowish solid (111 mg, 0.29 mmol, 99%).

Analytical Data $^1$H-NMR (300 MHz, DMSO-$d_6$): δ 9.49 (s, 1H), 8.47 (s, 1H), 8.13-8.03 (m, 4H), 7.83 (d, J=8.3 Hz, 2H), 7.70 (d, J=7.7 Hz, 1H), 7.58 (s, 1H), 7.51 (d, J=7.1 Hz, 1H), 7.43 (t, J=7.7 Hz, 1H), 7.28 (d, J=7.7 Hz, 1H), 2.56 (s, 3H). MS: M−1 386.

Example 35: Synthesis of 3-(4-(2'-methoxy-[1,1'-biphenyl]-4-yl)-1H-1,2,3-triazol-1-yl)benzoic acid (35)

The title compound is synthesized following the procedure described for Example 33. The crude product is purified by column chromatography using ethyl acetate/methanol 9:1 as eluent, yielding compound 35 as a white solid (24 mg, 0.06 mmol, 22%).

Analytical Data $^1$H-NMR (300 MHz, DMSO-$d_6$): δ 9.41 (s, 1H), 8.51 (s, 1H), 8.19 (d, J=7.7 Hz, 1H), 8.00 (d, J=7.7 Hz, 1H), 7.71-7.62 (m, 3H), 7.37-7.35 (m, 3H), 7.13-7.05 (m, 3H), 3.81 (s, 3H). MS: M+1 372.

Example 36: Synthesis of 3-(4-(3'-methoxy-[1,1'-biphenyl]-4-yl)-1H-1,2,3-triazol-1-yl)benzoic acid (36)

The title compound is synthesized following the procedure described for Example 33. The crude product is purified by column chromatography using ethyl acetate/methanol 9:1 as eluent, yielding compound 36 as a white solid (66 mg, 0.18 mmol, 61%).

Analytical Data $^1$H-NMR (300 MHz, DMSO-$d_6$): δ 9.53 (s, 1H), 8.50 (s, 1H), 8.25 (d, J=7.7 Hz, 1H), 8.07-8.05 (m, 3H), 7.84-7.75 (m, 3H), 7.40-7.27 (m, 3H), 6.96 (d, J=7.7, 1H), 3.84 (s, 3H). MS: M+1 372.

Example 37: Synthesis of 3-(4-(2',4'-dimethoxy-[1,1'-biphenyl]-4-yl)-1H-1,2,3-triazol-1-yl)benzoic acid (37)

The title compound is synthesized following the procedure described for Example 33. The crude product is purified by column chromatography using ethyl acetate/methanol 9:1 as eluent, yielding compound 37 as a yellow solid (114 mg, 0.28 mmol, 98%).

Analytical Data $^1$H-NMR (300 MHz, DMSO-$d_6$): δ 9.41 (s, 1H), 8.47 (s, 1H), 8.13 (d, J=7.4 Hz, 1H), 8.04 (d, J=7.4 Hz, 1H), 7.96 (d, J=7.1 Hz, 2H), 7.71 (d, J=6.6 Hz, 1H), 7.55 (d, J=7.1 Hz, 2H), 7.27 (t, J=7.4 Hz, 1H), 6.67-6.61 (m, 2H), 3.80 (s, 3H), 3.78 (s, 3H). MS: M+1 402.

Example 38: Synthesis of 3-(4-(3',5'-dimethoxy-[1,1'-biphenyl]-4-yl)-1H-1,2,3-triazol-1-yl)benzoic acid (38)

The title compound is synthesized following the procedure described for Example 33. The crude product is purified by column chromatography using ethyl acetate/methanol 9:1 as eluent, yielding compound 38 as a yellow solid (115 mg, 0.29 mmol, 99%).

Analytical Data $^1$H-NMR (300 MHz, DMSO-$d_6$): δ 9.50 (s, 1H), 8.50 (s, 1H), 8.14 (d, J=7.1 Hz, 1H), 8.06-8.04 (m, 3H), 7.82 (d, J=8.2 Hz, 2H), 7.70 (t, J=7.1 Hz, 1H), 6.94-6.87 (m, 2H), 6.52 (s, 1H), 3.82 (s, 3H), 3.78 (s, 3H) MS: M+1 402.

Example 39: Synthesis of 3-(4-(4-(benzo[d][1,3]dioxol-5-yl)phenyl)-1H-1,2,3-triazol-1-yl)benzoic acid (39)

The title compound is synthesized following the procedure described for Example 33. The crude product is purified by column chromatography using ether/ethyl acetate 1:9 as eluent, yielding compound 39 as a yellowish solid (65 mg, 0.17 mmol, 58%).

Analytical Data $^1$H-NMR (300 MHz, DMSO-$d_6$): δ 9.48 (s, 1H), 8.49 (s, 1H), 8.22 (d, J=8.2 Hz, 1H), 8.05-7.94 (m, 3H), 7.79-7.74 (m, 3H), 7.33 (s, 1H), 7.23 (t, J=8.2 Hz, 1H), 7.02 (d, J=8.2 Hz, 1H), 6.11 (s, 2H). MS: M+1 386.

Example 40: Synthesis of 3-(4-(4-(2,3-dihydrobenzo[b][1,4]dioxin-6-yl)phenyl)-1H-1,2,3-triazol-1-yl)benzoic acid (40)

The title compound is synthesized following the procedure described for Example 33. The crude product is purified by column chromatography using ethyl acetate as eluent, yielding compound 40 as a pale yellow solid (115 mg, 0.29 mmol, 99%).

Analytical Data $^1$H-NMR (300 MHz, DMSO-$d_6$): δ 9.49 (s, 1H), 8.49 (s, 1H), 8.22 (d, J=8.0 Hz, 1H), 8.02 (d, J=8.5 Hz, 2H), 7.79-7.77 (m, 3H), 7.27-7.22 (m, 3H), 6.95 (d, J=8.0 Hz, 1H), 4.34-4.28 (m, 4H). MS: M+1 400.

Example 41: Synthesis of 3-(4-(3',4'-dimethoxy-[1,1'-biphenyl]-4-yl)-1H-1,2,3-triazol-1-yl)benzoic acid (41)

The title compound is synthesized following the procedure described for Example 33. The crude product is purified by column chromatography using ethyl acetate/methanol 9:1 and ethyl acetate/methanol 8:2 as eluents, yielding compound 41 as a white solid (65 mg, 0.16 mmol, 56%).

Analytical Data $^1$H-NMR (300 MHz, DMSO-$d_6$): δ 9.41 (s, 1H), 8.49 (s, 1H), 8.16 (d, J=7.9 Hz, 1H), 8.08-8.02 (m, 3H), 7.79 (d, J=8.0 Hz, 2H), 7.71 (t, J=7.9 Hz. 1H), 7.30-7.27 (m, 2H), 7.06 (d, J=7.9 Hz, 1H), 3.88 (s, 3H), 3.82 (s, 3H). MS: M+1 402.

Example 42: Synthesis of 3-(4-(2',3'-dimethoxy-[1,1'-biphenyl]-4-yl)-1H-1,2,3-triazol-1-yl)benzoic acid (42)

The title compound is synthesized following the procedure described for Example 33. The crude product is purified by column chromatography using ethyl acetate/methanol 9:1 and ethyl acetate/methanol 8:2 as eluents, yielding compound 42 as a white solid (88 mg, 0.22 mmol, 76%).

Analytical Data $^1$H-NMR (300 MHz, DMSO-$d_6$): δ 9.53 (s, 1H), 8.56 (s, 1H), 8.18-8.07 (m, 4H), 7.77 (t, J=7.6 Hz, 1H), 7.66 (d, J=7.3 Hz, 2H), 7.21-7.15 (m, 2H), 7.03 (d, J=7.6 Hz, 1H), 3.91 (s, 3H), 3.62 (s, 3H). MS: M+1 402.

Example 43: Synthesis of 3-(4-(4-(2,3-dihydrobenzo[b][1,4]dioxin-5-yl)phenyl)-1H-1,2,3-triazol-1-yl)benzoic acid (43)

The title compound is synthesized following the procedure described for Example 33. The crude product is purified by column chromatography using ethyl acetate/methanol 9:1 and ethyl acetate/methanol 8:2 as eluents, yielding compound 43 as a pale yellow solid (105 mg, 0.26 mmol, 91%).

Analytical Data $^1$H-NMR (300 MHz, DMSO-$d_6$): δ 9.42 (s, 1H), 8.49 (s, 1H), 8.11-7.99 (m, 4H), 7.70 (t, J=7.2 Hz, 1H), 7.63 (d, J=7.4 Hz, 2H), 6.93-6.90 (m, 3H), 4.29-4.26 (m, 4H). MS: M+1 400.

Example 44: Synthesis of 3-(4-(2',6'-dimethoxy-[1,1'-biphenyl]-4-yl)-1H-1,2,3-triazol-1-yl)benzoic acid (44)

The title compound is synthesized following the procedure described for Example 33. The crude product is purified by column chromatography using ethyl acetate, ethyl acetate/methanol 9:1 and ethyl acetate/methanol 8:2 as eluents, yielding compound 44 as a pale yellow solid (53 mg, 0.13 mmol, 46%).

Analytical Data $^1$H-NMR (300 MHz, DMSO-$d_6$): δ 9.40 (s, 1H), 8.55 (s, 1H), 8.15 (d, J=7.4 Hz, 1H), 8.06 (d, J=7.4 Hz, 1H), 7.96-7.92 (m, 3H), 7.72-7.70 (m, 4H), 7.29 (t, J=7.4 Hz, 1H), 3.69 (s, 6H). MS: M+1 402.

Example 45: Synthesis of 3-(4-(2'-fluoro-5'-methoxy-[1,1'-biphenyl]-4-yl)-1H-1,2,3-triazol-1-yl)benzoic acid (45)

The title compound is synthesized following the procedure described for Example 33. The crude product is purified by column chromatography using petroleum ether/ethyl acetate 2:8 as eluent, yielding compound 45 as a yellow solid (46 mg, 0.12 mmol, 41%).

Analytical Data $^1$H-NMR (300 MHz, DMSO-$d_6$): δ 9.49 (s, 1H), 8.50 (s, 1H), 8.24 (d, J=7.9 Hz, 1H), 8.08-8.06 (m, 3H), 7.80-7.70 (m, 3H), 7.25 (t, J=7.1 Hz, 1H), 7.12-7.11 (m, 1H), 6.99-6.98 (m, 1H), 3.78 (s, 3H). MS: M+1 390.

Example 46: Synthesis of 3-(4-(2',5'-dimethoxy-[1,1'-biphenyl]-4-yl)-1H-1,2,3-triazol-1-yl)benzoic acid (46)

To a suspension of 4'-ethynyl-2,5-dimethoxy-1,1'-biphenyl (100 mg, 0.42 mmol) in water (425 μL) and t-BuOH (425 μL) 3-azidobenzoic acid (68 mg, 0.42 mmol) is added. Then, 42 μL of an aqueous solution of sodium ascorbate 1M and copper sulfate pentahydrate (1.04 mg, 0.0042 mmol) are added and the mixture is vigorously stirred overnight. The volatile is then removed and the crude product is purified by column chromatography using petroleum ether/ethyl acetate 3:7 as eluent, yielding compound 46 as a yellowish solid (167 mg, 0.42 mmol, 99%).

Analytical Data $^1$H-NMR (300 MHz, $(CD_3)_2CO$): δ 9.18 (s, 1H), 8.58 (s, 1H), 8.26 (d, J=8.0 Hz, 1H), 8.15 (d, J=8.0 Hz, 1H), 8.05 (d, J=6.9 Hz, 2H), 7.77 (t, J=8.0 Hz, 1H), 7.65 (d, J=6.9 Hz, 2H), 7.04 (d, J=9.0 Hz, 1H), 6.97-6.89 (m, 2H), 3.80 (s, 3H), 3.76 (s, 3H). MS: M+1 402.

Example 47: Synthesis of methyl 4-(4-(2',5'-dimethoxy-[1,1'-biphenyl]-4-yl)-1H-1,2,3-triazol-1-yl) picolinate (47)

The title compound is synthesized following the procedure described for Example 46. The crude product is purified by column chromatography using petroleum ether/ethyl acetate 4:6 as eluent, yielding compound 47 as a yellowish solid (107 mg, 0.26 mmol, 61%).

Analytical Data $^1$H-NMR (300 MHz, $(CD_3)_2CO$): δ 9.38 (s, 1H), 8.93 (d, J=4.6 Hz, 1H) 8.65 (s, 1H), 8.26 (d, J=9.0 Hz, 1H) 8.05 (d, J=8.3 Hz, 2H), 7.67 (d, J=8.3 Hz, 2H), 7.05 (d, J=9.0 Hz, 1H), 6.95-6.91 (m, 2H), 4.03 (s, 3H), 3.81 (s, 3H), 3.77 (s, 3H). MS: M+1 417.

Example 48: Synthesis of 4-(4-(2',5'-dimethoxy-[1,1'-biphenyl]-4-yl)-1H-1,2,3-triazol-1-yl)picolinic acid (48)

Compound 47 (49 mg, 0.12 mmol) is solubilized in acetone (490 μL) and water (490 μL). NaOH (9.6 mg, 0.24 mmol) is added and the mixture is stirred at room temperature for 2 h. The volatile is then removed and the crude product is purified by column chromatography using ethyl acetate/methanol 8:2 and ethyl acetate/methanol 7:3 as eluents, yielding compound 48 as a pale yellow solid (36 mg, 0.09 mmol, 75%).

Analytical Data $^1$H-NMR (300 MHz, DMSO-$d_6$): δ 9.71 (s, 1H), 8.70-8.62 (m, 3H), 8.02 (d, J=8.0 Hz, 2H), 7.63 (d, J=8.0 Hz, 2H), 7.09 (d, J=9.6 Hz, 1H), 6.94-6.92 (m, 2H), 3.80 (s, 3H), 3.76 (s, 3H). MS: M+1 403.

Example 49: Synthesis of 4-(4-(2',5'-dimethoxy-[1,1'-biphenyl]-4-yl)-1H-1,2,3-triazol-1-yl)-3-fluoropyridine (49)

The title compound is synthesized following the procedure described for Example 46. The crude product is purified by column chromatography using petroleum ether/ethyl acetate 7:3 as eluent, yielding compound 49 as a yellow solid (95 mg, 0.25 mmol, 60%).

Analytical Data $^1$H-NMR (300 MHz, $CDCl_3$): δ 8.75 (s, 1H), 8.64 (d, J=6.0 Hz, 1H), 8.48 (s, 1H), 8.22 (d, J=6.0 Hz, 1H), 7.96 (d, J=8.3 Hz, 2H), 7.66 (d, J=8.3 Hz, 2H), 6.96-6.89 (m, 3H), 3.82 (s, 3H), 3.76 (s, 3H). MS: M+1 377.

Example 50: Synthesis of 4-(4-(2',5'-dimethoxy-[1,1'-biphenyl]-4-yl)-1H-1,2,3-triazol-1-yl)pyridine (50)

The title compound is synthesized following the procedure described for Example 46. The crude product is purified by column chromatography using petroleum ether/ethyl acetate 9:1 as eluent, yielding compound 50 as a yellow solid (119 mg, 0.33 mmol, 79%).

Analytical Data $^1$H-NMR (300 MHz, DMSO-$d_6$): δ 9.55 (s, 1H), 8.85 (s, 1H), 8.04-8.01 (m, 2H), 7.99 (d, J=8.3 Hz, 2H), 7.66 (d, J=8.3 Hz, 2H), 7.06 (d, J=6.9 Hz, 1H) 6.94-9.93 (m, 3H), 3.77 (s, 3H), 3.74 (s, 3H). MS: M+1 359.

Example 51: Synthesis of 3-(4-(2',5'-Dimethoxy-[1,1'-biphenyl]-4-yl)-1H-1,2,3-triazol-1-yl)pyridine (51)

The title compound is synthesized following the procedure described for Example 46. The crude product is purified by column chromatography using petroleum ether/ethyl acetate 5:5 as eluent, yielding compound 51 as a yellowish solid (117 mg, 0.33 mmol, 78%).

Analytical Data $^1$H-NMR (300 MHz, $CDCl_3$): δ 9.08 (s, 1H), 8.72 (s, 1H), 8.27-8.21 (m, 2H), 7.95 (d, J=8.3 Hz, 2H), 7.65 (d, J=8.3 Hz, 2H), 7.53 (t, J=5.2 Hz, 1H), 6.96-6.88 (m, 3H), 3.82 (s, 3H), 3.78 (s, 3H). MS: M+1 359.

Biological Assays

Figure 1:
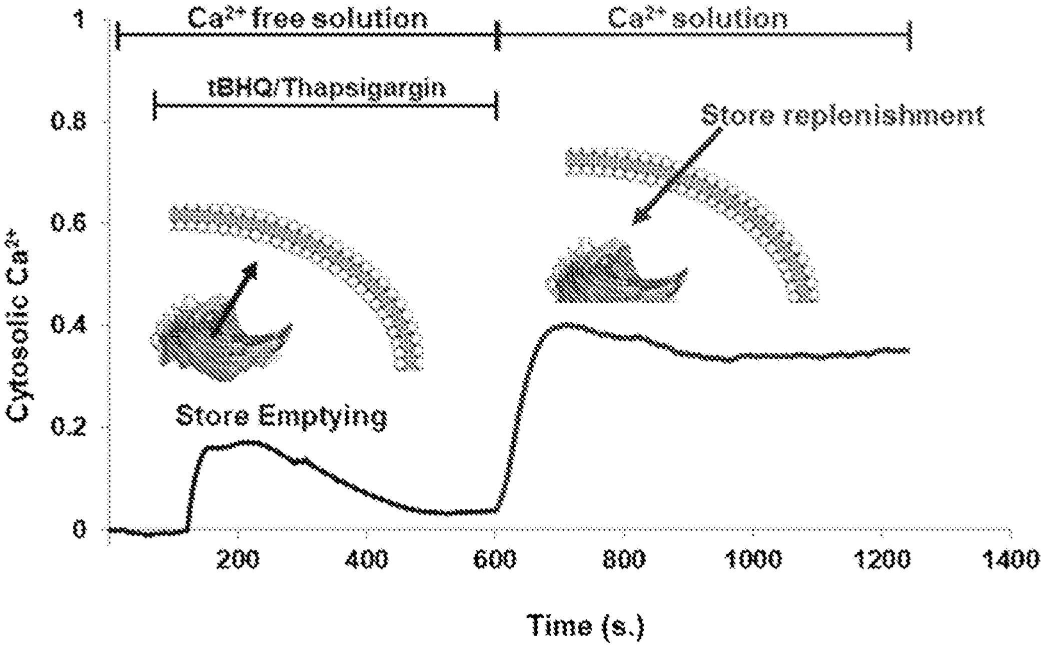
FIG. 1: Representative trace of Store Operated Calcium Entry (SOCE).

The key experiment to exemplify store-operated $Ca^{2+}$-entry (SOCE), as it is referred to nowadays, is depicted in FIG. 1. In brief, emptying of the ER/SR store leads to opening of a plasma membrane channel through which $Ca^{2+}$ can flow back in the cell and these two phenomena can be dissected by adding $Ca^{2+}$ to the extracellular solution after the intracellular stores are depleted. This simple yet powerful experimental approach remains valid to unmask the phenomenon in screenings.

Cell Cultures and Animal Models

Human embryonic kidney HEK cells were obtained from ATCC (ATCC® CRL-1573™, Rockville, MD, USA) and were cultured in Dulbecco's Modified Eagle's Medium (DMEM; Sigma-Aldrich, Italy), supplemented with 10% heat-inactivated FBS (Gibco, Italy), 1-glutamine 50 mg/mL (Sigma-Aldrich, Italy), penicillin 10 U/mL and streptomycin 100 mg/mL (Sigma-Aldrich, Italy) at 37° C., under a 5% $CO_2$ humidified atmosphere. For experiments, the cells were plated onto glass coverslips at concentrations of $5\times10^4$ per mL (24 mm diameter coverslips in 6 well plates).

In order to demonstrate the effect of the compounds and to develop a therapeutic strategy for gain-of function rare genetic disorders, we have generated a mouse colony bearing the p.I115F knock-in point mutation (KI-STIM1$^{I115F}$) on a C57B1/6N background. Furthermore, to evaluate the effects of the compounds on Duchenne muscular dystrophy, we used dystrophin-deficient mdx mice (C57BL/10ScSn-Dmdmdx/J) purchased from The Jackson Laboratory.

The care and husbandry of animals were in conformity with the institutional guidelines, in compliance with national and international laws and policies. Mice were housed in ventilated cages in 22±1° C. monitored rooms with 12 h light/dark cycles, had access to food and water ad libitum, and were weaned at 23 days by sex. The procedures were approved by the local animal-health and ethical committee (Università del Piemonte Orientale) and authorized by the national authority (Istituto Superiore di Sanità; authorization number N. 194/2019-PR).

KI-STIM$^{I115F}$ founders in a C57B1/6N background were obtained from PolyGene transgenics (CH, https://www.polygene.ch/). Briefly, this knock-in mouse model was generated by homologous recombination in electroporation-transfected embryonic stem (ES) cells on exon 3 of the Stim1 gene, located on chromosome 7, inserting the c.343A>T mutation (corresponding to isoleucine to phenylalanine substitution; I115F).

The linearized targeting vector F118.3 TV (FIG. 7), with a FRT-flanked neomycin resistance cassette, inserted in an unsuspicious region in intron 3 of Stim1, was used for the electroporation.

The integrity of the targeting vector was confirmed by sequencing exonic regions and by restriction analysis, using the following restriction enzymes: HindIII (7.2 kb/2.9 kb/1.7 kb/1.2 kb), PstI (8.3 kb/2.7 kb/1.3 kb/0.7 kb), PvuII (3.5 kb/2.8 kb/2.5 kb/1.1 kb/0.9 kb/0.8 kb/0.6 kb/0.4 kb/0.3 kb/0.15 kb) and BglII (5.5 kb/2.9 kb/2.2 kb/1.3 kb/1.0 kb/0.05 kb). G418 selection was used to maintain stable transfection, the clones obtained were analysed and validated by PCR and Southern blot using the restriction enzyme BstEII and a 3' external probe (LA probe). This probe has a size of 463 bp and was generated using the following primers:

```
F118.20
                                   (SEQ ID No.: 1)
5'-TGCCAGTTTCCCTATCAG-3';

F118.21
                                   (SEQ ID No.: 2)
5'-CCTAAGGATGGGATGTAACC-3.
```

The selected ES clones were injected into 49 blastocysts from grey C57B1/6N mice. Forty-one surviving blastocysts were transferred into two CD-1 foster mice. Resulting chimeras were mated to grey Flp-deleter mice. The offspring from the chimeras was screened for the Flp-mediated deletion of the neomycin cassette and the corresponding presence of the remaining FRT site.

Mice were identified with the ear punch method at weaning and the piece of tissue obtained was used to perform the genotyping using PCRBIO Rapid Extract PCR Kit (PCR Biosystems, UK). The DNA extraction was performed according to the manufacturer's instructions (5× PCRBIO Rapid Extract Buffer A, 10× PCRBIO Rapid Extract Buffer B).

Wild-type and KI-STIM1$^{I115F}$ primary myoblast were obtained from the following muscles: gastrocnemius, tibialis anterior, quadriceps femoris, extensor digitorum longus, soleus, biceps brachii and diaphragm. Each muscle was placed in a 60 mm dish in phosphate-buffered saline (PBS), removed from the tendon and separated longitudinally and subsequently chopped into smaller pieces. The small fragments were incubated with Pronase® (Protease, *Streptomyces griseus*, Calbiochem®, 25 KU) for 1 hour at 37° C. in shaking and neutralized with Dulbecco's Modified Eagle's Medium (DMEM, Sigma-Aldrich, Italy), supplemented with 10% heat-inactivated FCS (Gibco, Italy), L-glutamine 50 mg/mL (Sigma-Aldrich, Italy), penicillin 10 U/mL and streptomycin 100 mg/mL (Sigma-Aldrich, Italy), and 1% chicken embryo extract (Sigma-Aldrich, Italy). Tissues were then chopped into smaller pieces passing through pipets of 10 and 5 mL and the supernatant obtained was filtered in 40 μm strainer and centrifuge at RT for 10 minutes at 1200 rpm. The pellets were re-suspended and myoblasts were plated in a 100 mm dish in DMEM, supplemented with 10% heat-inactivated Fetal Bovine Serum (Gibco, Italy), L-glutamine 50 mg/mL (Sigma-Aldrich, Italy), penicillin 10 U/mL, streptomycin 100 mg/mL (Sigma-Aldrich, Italy), and 1% Chicken embryo extract (Sigma-Aldrich, Italy) for 90 minutes at 37° C., under a 5% $CO_2$ humidified atmosphere, for letting the debris. Supernatants were then centrifuged and plated in 2% gelatine-treated 35 mm dish in DMEM (Sigma-Aldrich, Italy), supplanted with 20% heat-inactivated Fetal Bovine Serum (Gibco, Italy), 10% Horse Serum (Gibco, Italy), L-glutamine 50 mg/mL (Sigma-Aldrich, Italy), penicillin 10 U/mL and streptomycin 100 mg/mL (Sigma-Aldrich, Italy), 1% chicken embryo extract (Sigma-Aldrich, Italy) and FGF 10 ng/ml (Peprotech, UK) at 37° C., under a 5% $CO_2$ humidified atmosphere for 6-7 days with a medium change every 24-36 hours. For differentiation into myotubes, myoblasts were transferred for 24 hours into differentiation medium consisting of DMEM with 5% horse serum and 1% penicillin-streptomycin.

For experiments, myotubes were further maintained in the same medium for a further 24 hours upon plating onto glass coverslips at a concentration of 20×10$^4$ per well (24 mm diameter coverslips in 6 well plates) and maintained in DMEM supplemented with 10% heat-inactivated FBS (Gibco, Italy), L-glutamine 50 mg/mL (Sigma-Aldrich, Italy), penicillin 10 U/mL and streptomycin 100 mg/mL (Sigma-Aldrich, Italy), at 37° C. under a 5% $CO_2$ humidified atmosphere. Experiments were performed 6-7 days after the extraction at P2 and P3.

Biological Evaluation of Compounds Targeting SOCE by Fura-2 $Ca^{2+}$ Measurements Compounds were tested on Hek cells in single-cell analysis using Fura-2 AM on cover-slips. Hek cells were loaded with 5 μM Fura-2 AM in presence of 0.02% of Pluronic-127 (both from Life Technologies, Italy) and 10 μM sulfinpyrazone in Krebs-Ringer buffer (KRB, 135 mM NaCl, 5 mM KCl, 0.4 mM $KH_2PO_4$, 1 mM $MgSO_4$, 5.5 mM glucose, 20 mM HEPES, pH 7.4) containing 2 mM $CaCl_2$ (30 min, room temperature). Afterwards, cells were washed and incubated with KRB for other 30 min to allow de-esterification of Fura-2AM. To measure store operated calcium entry, changes in cytosolic $Ca^{2+}$ were monitored upon depletion of the intracellular $Ca^{2+}$ stores. Experiments were carried out prior to and during exposure of the cells to the $Ca^{2+}$-free solution. In the absence of $Ca^{2+}$, the intracellular $Ca^{2+}$ stores were depleted by inhibition of the vesicular $Ca^{2+}$ pump by 2,5-t-butylhydroquinone (tBHQ, 50 μM; Sigma-Aldrich, Italy). Re-addition of 2 mM $Ca^{2+}$ allowed assessing the SOCE. During the experiments the cover-slips were mounted into acquisition chamber and placed on the stage of a Leica DMI6000 epi-fluorescent microscope equipped with S Fluor×40/1.3 objective. Fura-2 was excited by alternate 340 and 380 nm using a Polychrome IV mono-chromator (Till Photon-ics, Germany) and the probe emission light was filtered through 520/20 band-pass filter and collected by a cooled CCD camera (Hamamatsu, Japan). The fluorescence signals were acquired and processed using MetaFluor software (Molecular Device, Sun-Nyvale, CA, USA). To quantify the differences in the amplitudes of $Ca^{2+}$ transients the ratio values were normalized using the formula ΔF/F0.

The percentage of SOCE modulation of the compounds was determined based on value of tBHQ-induced calcium influx into Hek cells. Data were analysed using Microsoft Excel and GraphPad Prism. Examples are presented in Table 2.

TABLE 2

| Hek Cells | |
|---|---|
| Compound name and (number) | % Inhibition |
| 3-(1-(3'-(Methylthio)-[1,1'-biphenyl]-4-yl)-1H-1,2,3-triazol-4-yl)benzoic acid (11) | 72.6 ± 13.6 (10 μM) |
| 3-(1-(2'-Methoxy-[1,1'-biphenyl]-4-yl)-1H-1,2,3-triazol-4-yl)benzoic acid (12) | 47.2 ± 7.2 (10 μM) |
| 3-(1-(3'-Methoxy-[1,1'-biphenyl]-4-yl)-1H-1,2,3-triazol-4-yl)benzoic acid (13) | 85.0 ± 9.0 (3 μM) |
| 3-(1-(2',4'-Dimethoxy-[1,1'-biphenyl]-4-yl)-1H-1,2,3-triazol-4-yl)benzoic acid (15) | 68.1 ± 4.2 (10 μM)<br>56.4 ± 21.0 (3 μM) |
| 3-(1-(3',5'-Dimethoxy-[1,1'-biphenyl]-4-yl)-1H-1,2,3-triazol-4-yl)benzoic acid (16) | 77.4 ± 4.7 (10 μM)<br>73.8 ± 11.3 (3 μM) |
| 3-(1-(4-(Benzo[d][1,3]dioxol-5-yl)phenyl)-1H-1,2,3-triazol-4-yl)benzoic acid (17) | 37.3 ± 4.2 (10 μM) |
| 3-(1-(4-(2,3-Dihydrobenzo[b][1,4]dioxin-6-yl)phenyl)-1H-1,2,3-triazol-4-yl)benzoic acid (18) | 82.7 ± 4.0 (10 μM)<br>77.5 ± 8.2 (3 μM) |
| 3-(1-(3',4'-Dimethoxy-[1,1'-biphenyl]-4-yl)-1H-1,2,3-triazol-4-yl)benzoic acid (19) | 54.3 ± 6.3 (3 μM) |

TABLE 2-continued

| Hek Cells | |
|---|---|
| Compound name and (number) | % Inhibition |
| 3-(1-(2',3'-Dimethoxy-[1,1'-biphenyl]-4-yl)-1H-1,2,3-triazol-4-yl)benzoic acid (20) | 96.5 ± 2.4 (3 μM) |
| 3-(1-(4-(2,3-Dihydrobenzo[b][1,4]dioxin-5-yl)phenyl)-1H-1,2,3-triazol-4-yl)benzoic acid (21) | 70.9 ± 7.9 (3 μM) |
| 3-(1-(2'-Fluoro-5'-methoxy-[1,1'-biphenyl]-4-yl)-1H-1,2,3-triazol-4-yl)benzoic acid (23) | 74.7 ± 6.3 (3 μM) |
| 3-(1-(2',5'-Dimethoxy-[1,1'-biphenyl]-4-yl)-1H-1,2,3-triazol-4-yl)benzoic acid (24) | 85.8 ± 6.5 (3 μM) |
| 4-(1-(2',5'-Dimethoxy-[1,1'-biphenyl]-4-yl)-1H-1,2,3-triazol-4-yl)picolinic acid (25) | 79.9 ± 4.1 (10 μM) |
| 3-(4-(2'-Methoxy-[1,1'-biphenyl]-4-yl)-1H-1,2,3-triazol-1-yl)benzoic acid (35) | 59.6 ± 5.43 (10 μM) |
| 3-(4-(3'-Methoxy-[1,1'-biphenyl]-4-yl)-1H-1,2,3-triazol-1-yl)benzoic acid (36) | 87.0 ± 1.1 (10 μM) |
| 3-(4-(2',4'-Dimethoxy-[1,1'-biphenyl]-4-yl)-1H-1,2,3-triazol-1-yl)benzoic acid (37) | 77.1 ± 0.9 (10 μM)<br>53.0 ± 3.8 (3 μM) |
| 3-(4-(3',5'-Dimethoxy-[1,1'-biphenyl]-4-yl)-1H-1,2,3-triazol-1-yl)benzoic acid (38) | 86.2 ± 4.2 (10 μM) |
| 3-(4-(3',4'-Dimethoxy-[1,1'-biphenyl]-4-yl)-1H-1,2,3-triazol-1-yl)benzoic acid (41) | 39.6 ± 7.6 (3 μM) |
| 3-(4-(2',3'-Dimethoxy-[1,1'-biphenyl]-4-yl)-1H-1,2,3-triazol-1-yl)benzoic acid (42) | 93.2 ± 5.1 (3 μM) |
| 3-(4-(4-(2,3-Dihydrobenzo[b][1,4]dioxin-5-yl)phenyl)-1H-1,2,3-triazol-1-yl)benzoic acid (43) | 44.1 ± 17.1 (3 μM) |
| 3-(4-(2'-Fluoro-5'-methoxy-[1,1'-biphenyl]-4-yl)-1H-1,2,3-triazol-1-yl)benzoic acid (45) | 88.9 ± 7.5 (3 μM) |
| 3-(4-(2',5'-Dimethoxy-[1,1'-biphenyl]-4-yl)-1H-1,2,3-triazol-1-yl)benzoic acid (46) | 87.8 ± 2.9 (10 μM)<br>78.7 ± 3.8 (3 μM) |
| Methyl 4-(4-(2',5'-dimethoxy-[1,1'-biphenyl]-4-yl)-1H-1,2,3-triazol-1-yl)picolinate (47) | 73.5 ± 1.4 (10 μM) |
| 4-(4-(2',5'-Dimethoxy-[1,1'-biphenyl]-4-yl)-1H-1,2,3-triazol-1-yl)picolinic acid (48) | 57.2 ± 8.3 (10 μM) |

TABLE 3

| Hek Cells | |
|---|---|
| Compound name and (number) | Residual activity of SOCE |
| 3-(4-(2',6'-Dimethoxy-[1,1'-biphenyl]-4-yl)-1H-1,2,3-triazol-1-yl)benzoic acid (44) | 122.79 ± 0.89 (3 μM) |

Pharmacological Modulation of SOCE in Myotubes from STIM1 Mutated Mouse Model (M-STIM1$^{I115F}$)

Myotubes were generated from 4 animals in each condition. We also analysed whether SOCE in WT myotubes was modified during the lifespan of these animals. To do this, we employed a classical protocol for $Ca^{2+}$-entry, in which stores are depleted with tBHQ in a $Ca^{2+}$-free buffer and after 10 minutes cells are perfused in a $Ca^{2+}$-containing solution (2 mM).

Myotubes from 4 wild type (WT) and 4 KI-STIM1$^{I115F}$ mice were loaded with 5 μM Fura-2 AM and placed in an extracellular solution containing 0 mM $Ca^{2+}$. Stores were depleted with 50 μM tBHQ and after 10 minutes cells are perfused in a $Ca^{2+}$-containing solution (2 mM) in presence or absence of the selected compound (3-(1-(3'-methoxy-[1,1-biphenyl]-4-yl)-1H-1,2,3-triazol-4-yl)benzoic acid). As seen in FIG. 3, myotubes from KI-STIM1$^{I115F}$ display a significantly augmented SOCE compared to WT already at 1 month. The increased SOCE was retained throughout all time points examined (1, 3, 6 and 12 months). Interestingly, SOCE from WT myotubes appeared to be higher in younger animals (1 month) and decreased in the following time-points.

The effect of compound 3-(1-(4-(2,3-dihydrobenzo[b][1,4]dioxin-6-yl)phenyl)-1H-1,2,3-triazol-4-yl)benzoic acid on myotubes is presented in FIG. 4. As it can be observed, the compound is able to revert the over-activation of STIM1 mutated proteins (FIG. 4).

Pharmacological Modulation of SOCE from Myotubes of DMD Mouse Model (mdx)

Myotubes were generated from 4 animals in each condition. We analysed whether SOCE is increased in myotubes from mxd mice as compared to myotubes from WT mice. To do this, we employed a classical protocol for $Ca^{2+}$-entry, in which stores are depleted with tBHQ in a $Ca^{2+}$-free buffer and after 10 minutes cells are perfused in a $Ca^{2+}$-containing solution (2 mM).

Myotubes from 4 wild type (WT) and 4 mdx mice were loaded with 5 μM Fura-2 AM and placed in an extracellular solution containing 0 mM $Ca^{2+}$. Stores were depleted with 50 μM tBHQ and after 10 minutes cells are perfused in a $Ca^{2+}$-containing solution (2 mM) in presence or absence of the selected compound (3-(1-(3-methoxy-[1,1-biphenyl]-4-yl)-1H-1,2,3-triazol-4-yl)benzoic acid). As seen in FIG. 5, myotubes from mdx mice display a significantly augmented SOCE compared to WT already at 3 months.

The effect of compound 3-(1-(4-(2,3-Dihydrobenzo[b][1,4]dioxin-6-yl)phenyl)-1H-1,2,3-triazol-4-yl)benzoic acid on myotubes is presented in FIG. 6. As it can be observed, the compound is able to revert the over-activation of SOCE in DMD mouse model (FIG. 6).

The invention claimed is:

1. A compound of formula (I):

(I)

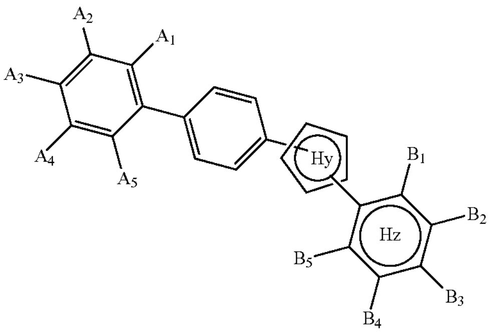

wherein ring Hy is selected from

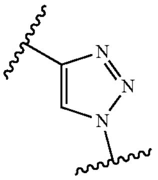 and 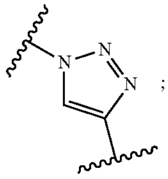 ;

ring Hz is selected from

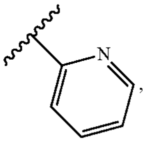, 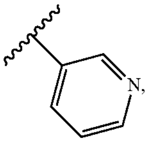

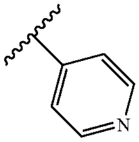 and 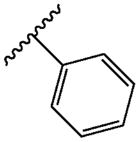 ;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHSO_2R_1$, $CONHR_1$, $CONR_1R_2$, $SO_2NHR_1$, COOH, $COOR_1$, $NO_2$, CN, and a 5-6 membered O-heterocyclic group;

$A_1$ and $A_2$, or $A_2$ and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are identical or different and independently selected from H, $CH_2COOH$, COOH, $COOR_3$, CN, $CF_3$, Br, I, Cl, F, and 1H-tetrazol-5-yl;

wherein $R_1$, $R_2$ and $R_3$ are selected from unsubstituted methyl, ethyl, tert-butyl, iso-propyl, pentan-2-yl, pyridine-4-yl, and benzyl;

provided that at least one of $A_1$, $A_2$, $A_3$, $A_4$ and $A_5$ is not H; and provided that at least one of $B_1$, $B_2$, $B_3$, $B_4$ and $B_5$ is not H;

and/or a pharmaceutically acceptable salt.

2. The compound according to claim 1, wherein, $A_1$ is selected from H, F, OMe, and a 5-6 membered O-heterocyclic group.

3. The compound according to claim 1, wherein $A_2$ is selected from H, OMe, SMe, OH, and a 5-6 membered O-heterocyclic group.

4. The compound according to claim 1, wherein $A_3$, $A_4$ and $A_5$ are independently selected from H, OMe, and a 5-6 membered O-heterocyclic group.

5. The compound according to claim 1, wherein two adjacent groups at position $A_1$, $A_2$, $A_3$, $A_4$ or As form together a 5-6 membered O-heterocyclic group fused with the phenyl ring to which they are attached, the heterocyclic group fused with the phenyl ring being selected from dihydrobenzodioxinyl or benzodioxolyl.

6. The compound according to claim 1, wherein $B_1$ and $B_5$ are independently selected from H and F.

7. The compound according to claim 1, wherein $B_2$ and $B_4$ are independently selected from H, $CH_2COOH$, COOH, COOMe, CN, and 1H-tetrazol-5-yl.

8. The compound according to claim 1, wherein $B_3$ is H.

9. The compound according to claim 1, selected from:

3-(1-(3'-(Methylthio)-[1,1'-biphenyl]-4-yl)-1H-1,2,3-triazol-4-yl) benzoic acid;

3-(1-(2'-Methoxy-[1,1'-biphenyl]-4-yl)-1H-1,2,3-triazol-4-yl) benzoic acid;

3-(1-(3'-Methoxy-[1,1'-biphenyl]-4-yl)-1H-1,2,3-triazol-4-yl) benzoic acid;

3-(1-(3'-Hydroxy-[1,1'-biphenyl]-4-yl)-1H-1,2,3-triazol-4-yl) benzoic acid;

3-(1-(2',4'-Dimethoxy-[1,1'-biphenyl]-4-yl)-1H-1,2,3-triazol-4-yl) benzoic acid;

3-(1-(3',5'-Dimethoxy-[1,1'-biphenyl]-4-yl)-1H-1,2,3-triazol-4-yl) benzoic acid;

3-(1-(4-(Benzo[d][1,3]dioxol-5-yl) phenyl)-1H-1,2,3-triazol-4-yl) benzoic acid;

3-(1-(4-(2,3-Dihydrobenzo[b][1,4]dioxin-6-yl) phenyl)-1H-1,2,3-triazol-4-yl) benzoic acid;

3-(1-(3',4'-Dimethoxy-[1,1'-biphenyl]-4-yl)-1H-1,2,3-triazol-4-yl) benzoic acid;

3-(1-(2',3'-Dimethoxy-[1,1'-biphenyl]-4-yl)-1H-1,2,3-triazol-4-yl) benzoic acid;

3-(1-(4-(2,3-Dihydrobenzo[b][1,4]dioxin-5-yl) phenyl)-1H-1,2,3-triazol-4-yl) benzoic acid;

3-(1-(2',6'-Dimethoxy-[1,1'-biphenyl]-4-yl)-1H-1,2,3-triazol-4-yl) benzoic acid;

3-(1-(2'-Fluoro-5'-methoxy-[1,1'-biphenyl]-4-yl)-1H-1,2,3-triazol-4-yl) benzoic acid;

3-(1-(2',5'-Dimethoxy-[1,1'-biphenyl]-4-yl)-1H-1,2,3-triazol-4-yl) benzoic acid;

4-(1-(2',5'-Dimethoxy-[1,1'-biphenyl]-4-yl)-1H-1,2,3-triazol-4-yl) picolinic acid;

4-(1-(2',5'-Dimethoxy-[1,1'-biphenyl]-4-yl)-1H-1,2,3-triazol-4-yl)-3-fluoropyridine;

3-(1-(4-(2,3-Dihydrobenzo[b][1,4]dioxin-6-yl) phenyl)-1H-1,2,3-triazol-4-yl) benzonitrile;

5-(3-(1-(4-(2,3-Dihydrobenzo[b][1,4]dioxin-6-yl) phenyl)-1H-1,2,3-triazol-4-yl) phenyl)-1H-tetrazole;

2-(3-(1-(4-(2,3-Dihydrobenzo[b][1,4]dioxin-6-yl) phenyl)-1H-1,2,3-triazol-4-yl) phenyl) acetic acid;

3-(4-([1,1'-Biphenyl]-4-yl)-1H-1,2,3-triazol-1-yl) benzoic acid;

3-(4-(3'-(Methylthio)-[1,1'-biphenyl]-4-yl)-1H-1,2,3-triazol-1-yl) benzoic acid;

3-(4-(2'-Methoxy-[1,1'-biphenyl]-4-yl)-1H-1,2,3-triazol-1-yl) benzoic acid;

3-(4-(3'-Methoxy-[1,1'-biphenyl]-4-yl)-1H-1,2,3-triazol-1-yl) benzoic acid;

3-(4-(2',4'-Dimethoxy-[1,1'-biphenyl]-4-yl)-1H-1,2,3-triazol-1-yl) benzoic acid;

3-(4-(3',5'-Dimethoxy-[1,1'-biphenyl]-4-yl)-1H-1,2,3-triazol-1-yl) benzoic acid;

3-(4-(4-(Benzo[d][1,3]dioxol-5-yl) phenyl)-1H-1,2,3-triazol-1-yl) benzoic acid;

3-(4-(4-(2,3-Dihydrobenzo[b][1,4]dioxin-6-yl) phenyl)-1H-1,2,3-triazol-1-yl) benzoic acid;

3-(4-(3',4'-Dimethoxy-[1,1'-biphenyl]-4-yl)-1H-1,2,3-triazol-1-yl) benzoic acid;

3-(4-(2',3'-Dimethoxy-[1,1'-biphenyl]-4-yl)-1H-1,2,3-triazol-1-yl) benzoic acid;

3-(4-(4-(2,3-Dihydrobenzo[b][1,4]dioxin-5-yl) phenyl)-1H-1,2,3-triazol-1-yl) benzoic acid;

3-(4-(2',6'-Dimethoxy-[1,1'-biphenyl]-4-yl)-1H-1,2,3-triazol-1-yl) benzoic acid;

3-(4-(2'-Fluoro-5'-methoxy-[1,1'-biphenyl]-4-yl)-1H-1,2,3-triazol-1-yl) benzoic acid;

3-(4-(2',5'-Dimethoxy-[1,1'-biphenyl]-4-yl)-1H-1,2,3-triazol-1-yl) benzoic acid;

Methyl 4-(4-(2',5'-dimethoxy-[1,1'-biphenyl]-4-yl)-1H-1,2,3-triazol-1-yl) picolinate;

4-(4-(2',5'-Dimethoxy-[1,1'-biphenyl]-4-yl)-1H-1,2,3-triazol-1-yl) picolinic acid; and 4-(4-(2',5'-Dimethoxy-[1,1'-biphenyl]-4-yl)-1H-1,2,3-triazol-1-yl)-3-fluoropyridine.

10. A method for treatment of a patient suffering from a disease condition depending on increased/decreased activity of SOCE, comprising administering to the patient a compound of formula (I)

(I)

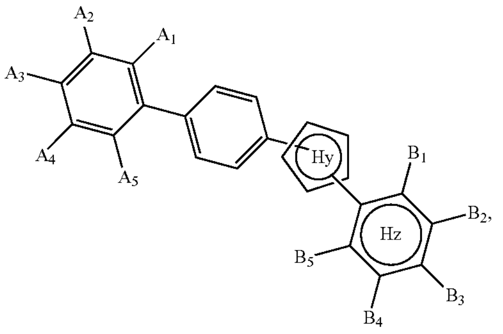

wherein ring Hy is selected from

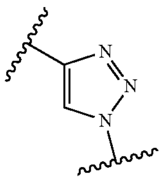

and

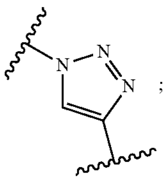

;

ring Hz is selected from

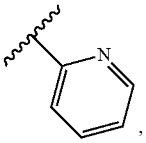

,

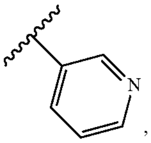

,

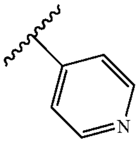

and

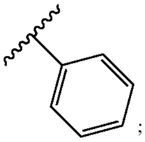

;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHSO_2R_1$, $CONHR_1$, $CONR_1R_2$, $SO_2NHR_1$, COOH, $COOR_1$, $NO_2$, CN, and a 5-6 membered O-heterocyclic group;

$A_1$ and $A_2$, or $A_2$ and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are identical or different and independently selected from H, $CH_2COOH$, COOH, $COOR_3$, CN, $CF_3$, Br, I, Cl, F, and 1H-tetrazol-5-yl;

$R_1$ and $R_2$ are identical or different from each other and independently selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;

$R_3$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heteroaryl, wherein m is an integer 1 to 4;

provided that at least one of $A_1$, $A_2$, $A_3$, $A_4$ and $A_5$ is not H; and provided that at least one of $B_1$, $B_2$, $B_3$, $B_4$ and $B_5$ is not H;

and/or a pharmaceutically acceptable salt.

11. A method for treatment of a patient suffering from diseases linked to loss- or gain-of-function STIM1/Orai1 mutations, muscular dystrophies, inflammatory diseases, comprising administering to the patient a compound of formula (I)

(I)

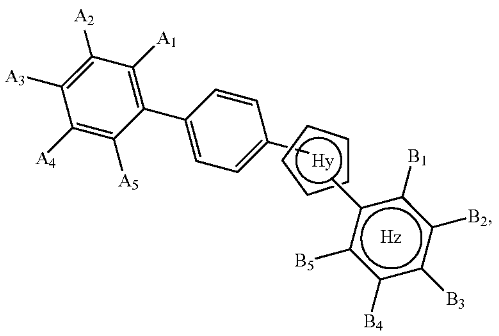

wherein ring Hy is selected from

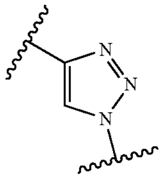 and 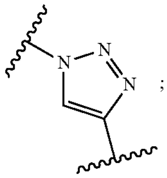 ;

ring Hz is selected from

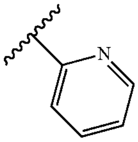 , 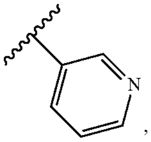 , 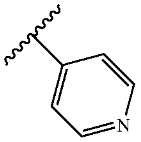 and

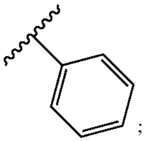 ;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHSO_2R_1$, $CONHR_1$, $CONR_1R_2$, $SO_2NHR_1$, COOH, $COOR_1$, $NO_2$, CN, and a 5-6 membered O-heterocyclic group;

$A_1$ and $A_2$, or $A_2$ and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are identical or different and independently selected from H, $CH_2COOH$, COOH, $COOR_3$, CN, $CF_3$, Br, I, Cl, F, and 1H-tetrazol-5-yl;

$R_1$ and $R_2$ are identical or different from each other and independently selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;

$R_3$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heteroaryl, wherein m is an integer 1 to 4;

provided that at least one of $A_1$, $A_2$, $A_3$, $A_4$ and $A_5$ is not H; and provided that at least one of $B_1$, $B_2$, $B_3$, $B_4$ and $B_5$ is not H;

and/or a pharmaceutically acceptable salt.

12. Pharmaceutical composition comprising at least one compound of formula (I) and a pharmaceutically acceptable carrier and/or vehicle (I)

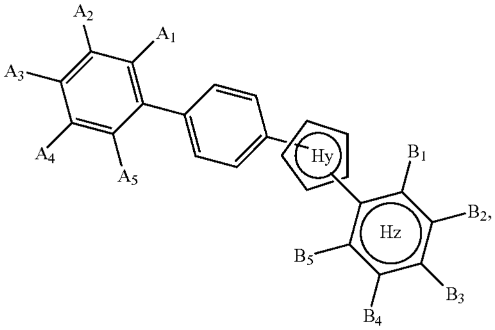

wherein ring Hy is selected from

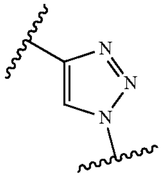 and 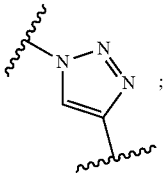 ;

ring Hz is selected from

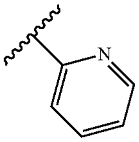 , 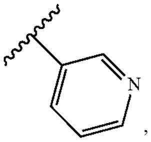 , 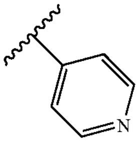 and

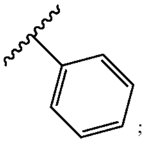 ;

$A_1$, $A_2$, $A_3$, $A_4$ and $A_5$ are identical or different from each other and independently selected from H, $CF_3$, Br, I, Cl, F, OH, $OR_1$, $SR_1$, $NH_2$, $NHR_1$, $NR_1R_2$, $S(O)R_1$, $S(O)_2R_1$, $NHSO_2R_1$, $CONHR_1$, $CONR_1R_2$, $SO_2NHR_1$, COOH, $COOR_1$, $NO_2$, CN, a 5-6 membered O-heterocyclic group;

$A_1$ and $A_2$, or Az and $A_3$, or $A_3$ and $A_4$, or $A_4$ and $A_5$ can form together a 5-6 membered O-heterocyclic group fused to the phenyl ring to which they are attached;

$B_1$, $B_2$, $B_3$, $B_4$ and $B_5$ are identical or different and independently selected from H, $CH_2COOH$, COOH, $COOR_3$, CN, $CF_3$, Br, I, Cl, F, 1H-tetrazol-5-yl;

$R_1$ and $R_2$ are identical or different from each other and independently selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;

$R_3$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heteroaryl, wherein m is an integer 1 to 4;

provided that at least one of $A_1$, $A_2$, $A_3$, $A_4$ and $A_5$ is not H; and provided that at least one of $B_1$, $B_2$, $B_3$, $B_4$ and $B_5$ is not H;

and/or a pharmaceutically acceptable salt.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: artificial
<220> FEATURE:
<223> OTHER INFORMATION: forward F118.20 primer

<400> SEQUENCE: 1

tgccagtttc cctatcag                                                     18


<210> SEQ ID NO 2
<211> LENGTH: 20
<212> TYPE: DNA
<213> ORGANISM: artificial
```

-continued

```
<220> FEATURE:
<223> OTHER INFORMATION: reverse F118.21 primer

<400> SEQUENCE: 2

cctaaggatg ggatgtaacc                                        20
```